US007820700B2

(12) United States Patent
Miyata et al.

(10) Patent No.: US 7,820,700 B2
(45) Date of Patent: Oct. 26, 2010

(54) 2-PHENYLPYRIDINE DERIVATIVE

(75) Inventors: Junji Miyata, Chuo-ku (JP); Ryo Naito, Chuo-ku (JP); Masakatsu Kawakami, Chuo-ku (JP); Toru Asano, Chuo-ku (JP)

(73) Assignee: Astellas Pharma Inc., Tokyo (JP)

( * ) Notice: Subject to any disclaimer, the term of this patent is extended or adjusted under 35 U.S.C. 154(b) by 903 days.

(21) Appl. No.: 11/661,284

(22) PCT Filed: Aug. 26, 2005

(86) PCT No.: PCT/JP2005/015549

§ 371 (c)(1),
(2), (4) Date: Feb. 27, 2007

(87) PCT Pub. No.: WO2006/022374

PCT Pub. Date: Mar. 2, 2006

(65) Prior Publication Data

US 2007/0275950 A1    Nov. 29, 2007

(30) Foreign Application Priority Data

Aug. 27, 2004  (JP)  ............................. 2004-249275
Mar. 17, 2005  (JP)  ............................. 2005-078222

(51) Int. Cl.
  *A61K 31/4418*  (2006.01)
  *C07D 213/79*  (2006.01)
(52) U.S. Cl. ...................... 514/354; 546/326
(58) Field of Classification Search ................. 514/354; 546/326
See application file for complete search history.

(56) References Cited

U.S. PATENT DOCUMENTS

| 3,655,679 A | 4/1972 | Tsung-Ying et al. |
| 3,703,582 A | 11/1972 | Tsung-Ying et al. |
| 4,346,094 A | 8/1982 | Beck et al. |
| 4,495,195 A | 1/1985 | Beck et al. |
| 4,544,752 A | 10/1985 | Beck et al. |
| 5,614,520 A | 3/1997 | Kondo et al. |
| 5,843,969 A | 12/1998 | Ota et al. |
| 6,015,829 A | 1/2000 | Ishibuchi et al. |
| 6,395,753 B1 * | 5/2002 | Kodama et al. ............. 514/318 |

FOREIGN PATENT DOCUMENTS

| JP | 57-85379 A | 5/1982 |
| JP | 59-095272 A | 6/1984 |
| JP | 06-065210 A | 3/1994 |
| JP | 06-211815 A | 8/1994 |
| JP | 10-310578 A | 11/1998 |
| JP | 2000-001431 A | 1/2000 |
| JP | 2002-105067 A | 4/2002 |
| WO | WO 92/09279 A1 | 6/1992 |
| WO | WO 96/31211 A1 | 10/1996 |
| WO | WO 98/18765 A1 | 5/1998 |
| WO | WO 02/098840 A1 | 12/2002 |
| WO | WO 03/020703 A1 | 3/2003 |

OTHER PUBLICATIONS

Cuisa et al. Influence of various pyridine derivatives on the elimination of uric acid, Annali di Chimica Applicate, 1931, vol. 21, p. 553-8, Chemical Abstract No. 26: 28808.
Walford et al. Ant inflammatory Analogs of Flufenisal, Journal of Medicinal Chemistry, 1971, col. 14, No. 4, p. 339-344.

* cited by examiner

*Primary Examiner*—Sharmila Gollamudi Landau
*Assistant Examiner*—Kortney L Klinkel
(74) *Attorney, Agent, or Firm*—Sughrue Mion, PLLC

(57) ABSTRACT

The present invention relates to a novel 2-phenylpyridine derivative or a salt thereof, wherein the pyridine ring is substituted with a carboxyl group or the like and the benzene ring has an electron-withdrawing group such as a cyano group and an electron-donating group such as a substituted alkoxy group at the same time.

Since the compound of the invention has good xanthine oxidase-inhibitory action and uric acid-lowering action and does not have a structure derived from nucleic acid, the compound has advantages of high safety and excellent effects as compared with conventional compounds and is useful as a therapeutic or preventive agent for hyperuricemia, gout, inflammatory bowel diseases, diabetic kidney diseases, diabetic retinopathy, or the like.

8 Claims, No Drawings

2-PHENYLPYRIDINE DERIVATIVE

This is a national stage application under 35 U.S.C. §371 of PCT/JP2005/015549 filed on Aug. 26, 2005, which claims priority from Japanese patent application P.2004-249275 filed on Aug. 27, 2004 and from Japanese patent application P.2005-078222 filed on Mar. 17, 2005, all of which are incorporated herein by reference.

TECHNICAL FIELD

The present invention relates to a 2-phenylpyridine derivative useful as a medicament, particularly a therapeutic or preventive agent for diseases in which xantine oxidase participates, such as hyperuricemia, gout, inflammatory bowel diseases, diabetic kidney diseases, and diabetic retinopathy.

BACKGROUND ART

Abnormal increase in blood uric acid level, i.e., hyperuricemia is a disease which closely relates to gout, renal dysfunction, urolithiasis, and the like (Shindan to Chiryo, 2002, 90(2), 244-248 and Shindan to Chiryo, 2002, 90(2), 220-224). Also, in organ transplantation (Ren. Fail. May 2002; 24(3): 361-7) and chemotherapy of cancers (Am. J. Health Syst. Pharm. Nov. 1, 2003; 60(21): 2213-22), it is known that serum uric acid level is remarkably increased and renal dysfunction is induced (tumor lysis syndrome and the like). The therapeutic drugs for hyperuricemia are roughly divided into uric acid-excretion accelerators and uric acid-synthesis inhibitors. However, since the action is reduced in the uric acid-excretion accelerators when renal function decreases, allopurinol (Nippon Rinsho, December 1996; 54(12): 3364-8 and Nippon Rinsho, 2003; 61, Suppl. 1: 197-20) which is a uric acid-synthesis inhibitor is suitably used for patients having decreased renal function (Guideline for therapy of hyperuricemia/gout, Japanese Society of Gout and Nucleic Acid Metabolism, Therapeutic Guideline 2002). Xanthine oxidase is an enzyme directing biosynthesis of uric acid, and xanthine oxidase inhibitors which inhibit the enzyme is effective, as uric acid-synthesis inhibitors, for therapy of hyperuricemia and various diseases attributable thereto. Allopurinol employed in clinical use is only one xanthine oxidase inhibitor which is in practical use, at present.

On the other hand, xanthine oxidase is known to have a role as an active oxygen-producing enzyme (Drug Metab. Rev. May 2004; 36(2): 363-75). Active oxygen is a exacerbation factor of morbid conditions, which causes DNA and cell damage and also induces inflammatory cytokine production (Free Radic. Biol. Med. May 15, 2001; 30(10): 1055-66). For example, it is known that active oxygen deeply participates in autoimmune and inflammatory diseases such as ulcerative colitis and Crohn's disease (Scand. J. Gastroenterol. December 2001; 36(12): 1289-94) and ischemic reperfusion disorder (Biochem. Biophys. Res. Commun. Mar. 5, 2004; 315(2): 455-62). Furthermore, recently, in diabetic kidney diseases (Curr. Med. Res. Opin. March 2004; 20(3): 369-79), heart failure (J. Physiol. Mar. 16, 2004; 555(Pt 3): 589-606, Epub 2003 Dex 23), cerebrovascular disorder (Stroke, April 1989; 20(4): 488-94), and the like, it is suggested that active oxygen participates in as one of exacerbation factors. Moreover, in diabetic retinopathy, it is known that an increase in vascular endothelial growth factor (VEGF) in the vitreous body deeply participates in morbid condition and an increase in expression of VEGF through oxidation stress occurs under morbid conditions (Curr Drug Targets. June 2005; 6(4): 511-24). Since a xanthine oxidase inhibitor inhibits production of active oxygen, it is effective in treatment of these diseases. Actually, it has been reported that allopurinol is effective in ulcerative colitis (Aliment. Pharmacol. Ther. September 2000; 14(9): 1159-62), angiopathy involved in diabetes (Hypertension, March 2000; 35(3): 746-51), and chronic heart failure (Circulation, Jul. 9, 2002; 106(2): 221-6) in human.

As above, although allopurinol which is a xanthine oxidase inhibitor is reported to have effectiveness for various diseases, severe adverse effects such as Stevens-Johnson syndrome, toxic epidermal necrolysis, hepatopathy, and renal dysfunction have been reported (Nippon Rinsho, 2003; 61, Suppl. 1: 197-201). As one cause thereof, it is pointed out that allopurinol has a nucleic acid-like structure and inhibits pyrimidine metabolic pathway (Life Sci. Apr. 14, 2000; 66(21): 2051-70). Accordingly, it is highly desired to develop a highly safe and highly effective xanthine oxidase inhibitor having a non-nucleic acid structure.

Hitherto, compounds having xanthine oxidase-inhibitory activity have been reported. For example, as xanthine oxidase inhibitors, there have been reported phenyl-substituted azole compounds such as 2-phenylthiazole derivatives (Patent Documents 1, 2, and 3), 3-phenylisothiazole derivatives (Patent Documents 4 and 5), 3-phenylpyrazole derivatives (Patent Documents 6, 7, and 8), 2-phenyloxazole derivatives (Patent Document 9), and 2-phenylimidazole derivatives (Patent Document 9).

On the other hand, it is described that a compound represented by the following formula (II) has a uric acid-excreting action and is useful for therapy of hyperuricemia (Non-Patent Document 1). However, there are neither disclosure nor suggestion of the xanthine oxidase-inhibitory action and uric acid-synthesis inhibitory action in the document.

[Chem. 1]

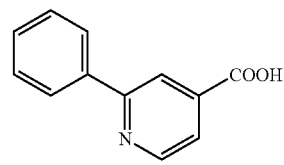

(II)

Moreover, it is suggested that a compound represented by the following general formula (III) is effective as antiinflammatory, antipyretic, analgesic, and diuretic agents (Patent Document 10).

[Chem. 2]

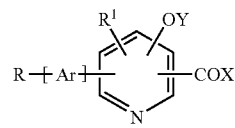

(III)

wherein the groups COX and OY are ortho to each other and [Ar] is para to either COX or OY; [Ar] represents benzene or the like, R represents alkyl, halogen, alkoxy, cyano, nitro, or the like, a halogen atom, lower alkyl, or the like, X represents —OH, —NH2, alkylamino, or the like, Y represents a hydrogen atom, alkyl, alkenyl, aralkyl, or the like, and $R^1$ represents a hydrogen atom or alkyl; see the publication for further information.

In addition, it is disclosed that a compound represented by the following formula (IV) has antiinflammatory and analgesic actions (Non-Patent Document 2).

[Chem. 3]

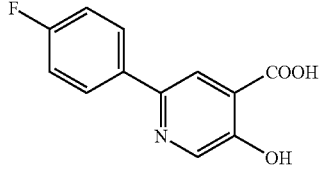

(IV)

However, in any of Patent Document 10 and Non-Patent Document 2, there are neither disclosure nor suggestion of the xanthine oxidase-inhibitory action and uric acid-synthesis inhibitory action.

Patent Document 1: WO92/09279
Patent Document 2: JP-A-2002-105067
Patent Document 3: WO96/31211
Patent Document 4: JP-A-57-85379
Patent Document 5: JP-A-6-211815
Patent Document 6: JP-A-59-95272
Patent Document 7: WO98/18765
Patent Document 8: JP-A-10-310578
Patent Document 9: JP-A-6-65210
Patent Document 10: DE2031230
Non-Patent Document 1: Annali di Chimica Applicata, Italy, 1931, Vol. 21, p. 553-558
Non-Patent Document 2: Journal of Medicinal Chemistry, USA, 1971, Vol. 14, p. 339-344

DISCLOSURE OF THE INVENTION

Problems that the Invention is to Solve

An object of the invention is to provide a highly safe and novel therapeutic or preventive agent for hyperuricemia, gout, inflammatory bowel diseases, diabetic kidney diseases, or diabetic retinopathy based on an excellent xanthine oxidase-inhibitory action.

Means for Solving the Problems

As a result of extensive studies on compounds having a xanthine oxidase-inhibitory action, although a xanthine oxidase-inhibitory action has been hitherto not known on 2-phenylpyridinecarboxylic acid derivatives, the present inventors have confirmed that a 2-phenylpyridine derivative represented by the following general formula wherein the pyridine ring is substituted with a carboxyl group or the like and the benzene ring has an electron-withdrawing group such as a cyano group and an electron-donating group such as a substituted alkoxy group at the same time has a strong xanthine oxidase-inhibitory action and uric acid-lowering action, antiinflammatory action, and the like based thereon and they have found that the derivative may be a good therapeutic or preventive agent for hyperuricemia, gout, inflammatory bowel diseases, diabetic kidney diseases, or diabetic retinopathy. Thus, they have accomplished the invention. Moreover, it has been confirmed that the compound of the invention has high safety. Furthermore, it has been surprisingly revealed that the compound of the invention also has an inhibitory activity of AKR1C3 which is one of aldo-keto reductases. Thus, it has been confirmed that the compound of the invention has a preferable action also as an antiinflammatory drug.

Namely, the invention relates to a novel 2-phenylpyridine derivative represented by the following general formula (I):

[Chem. 4]

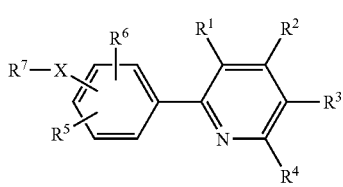

(I)

wherein the symbols have the following meanings:
$R^1$: H or halogen.
$R^2$: —$CO_2$H, —$CO_2$-lower alkyl or tetrazolyl group,
$R^3$ and $R^4$: the same or different from each other, H, halogen, or lower alkyl,
$R^5$: —CN, —$NO_2$, —Br, or halogeno-lower alkyl,
$R^6$: H, lower alkyl, —O-lower alkyl, halogen, or —CN,
X: —O—, —N($R^8$)—, or —S—,
where groups represented by $R^5$ and —X—$R^7$ are linked to meta- or para-position to the pyridyl group,
$R^8$: H or lower alkyl
$R^7$: linear or branched alkyl having 1 to 8 carbon atoms, linear or branched alkenyl having 3 to 8 carbon atoms, —Y-(cycloalkyl which may contain an oxygen atom), —Y-phenyl,
Y-naphthyl, or —Y-monocyclic or bicyclic heterocyclic group,
where the linear or branched alkyl having 1 to 8 carbon atoms and linear or branched alkenyl having 3 to 8 carbon atoms may be substituted with one to three groups selected from the groups shown in the following G1 group, which may be the same or different from each other, and the cycloalkyl which may contain an oxygen atom, phenyl, naphthyl, and monocyclic or bicyclic heterocyclic group may be substituted with one to four groups selected from the groups shown in the following G1 group and lower alkyl, which may be the same or different from each other,
G1 group: hydroxy, —CN, —O-lower alkyl, —S-lower alkyl, —$NR^9(R^{10})$, —(CO)$NR^9$ ($R^{10}$), —$CO_2$—$R^{11}$, and halogen,
Y: a bond, lower alkylene, lower alkenylene, -(lower alkylene)-O—, or -(lower alkylene)-O-(lower alkylene)-,
$R^9$, $R^{10}$, and $R^{11}$: the same or different from each other, H or lower alkyl,
where, when X is a group represented by —N($R^8$)—, $R^8$ and $R^7$ are combined together with the adjacent nitrogen atom to form a nitrogen-containing saturated heterocycle and the nitrogen-containing saturated heterocycle may be substituted with one or two groups selected from the following G2 group, which may be the same or different from each other,
G2 group: lower alkyl, hydroxy, —CN, —O-lower alkyl, —S-lower alkyl, halogen, —$NR^9(R^{10})$, —(CO)$NR^9(R^{10})$, —$CO_2$—$R^{11}$, phenyl, (cycloalkyl which may be substituted with lower alkyl), and —O-lower alkylene-cycloalkyl; the same shall apply hereinafter.

Moreover, the invention relates to a pharmaceutical composition comprising the 2-phenylpyridine derivative represented by the above general formula (I) or a pharmaceutically acceptable salt thereof and a pharmaceutically acceptable carrier. Preferably, it is the above pharmaceutical composition, which is a xanthine oxidase inhibitor and the above pharmaceutical composition, which is a preventive or therapeutic agent for hyperuricemia, gout, inflammatory bowel diseases, diabetic kidney diseases, or diabetic retinopathy.

Furthermore, the other embodiments are use of the 2-phenylpyridine derivative represented by the general formula (I) or a pharmaceutically acceptable salt thereof for the production of a preventive or therapeutic agent for hyperuricemia, gout, inflammatory bowel diseases, diabetic kidney diseases, or diabetic retinopathy and a preventive or therapeutic method of hyperuricemia, gout, inflammatory bowel diseases, diabetic kidney diseases, or diabetic retinopathy, which comprises administering a therapeutically effective amount of the 2-phenylpyridine derivative represented by the general formula (I) or a pharmaceutically acceptable salt thereof to a patient.

EFFECTS OF THE INVENTION

Since the compound of the invention has a potent xanthine oxidase-inhibitory action, the compound is useful as a therapeutic or preventive drug for hyperuricemia, gout, uric acid urolithiasis, renal dysfunction accompanied by hyperuricemia, inflammatory bowel diseases (ulcerative colitis, Crohn's disease), diabetic kidney diseases, diabetic retinopathy, organ damage at organ transplantation or ischemic reperfusion, tumor lysis syndrome, heart failure, and cerebrovascular disorder, particularly hyperuricemia, gout, inflammatory bowel diseases, diabetic kidney diseases, and diabetic retinopathy.

Namely, as mentioned below, the compound of the invention has an excellent uric acid-lowering action. The compound of the invention is also effective in patients whose renal function has decreased unlike ureic acid-excreting agents. Moreover, the compound has an excellent antiinflammatory action by suppressing formation of active oxygen produced via xanthine oxidase and by inhibiting AKR1C3. Furthermore, since the present compound can avoid adverse effects based on pyrimidine metabolic pathway inhibition, it has an excellent profile as compared with existing xanthine oxidase inhibitors such as allopurinol.

BEST MODE FOR CARRYING OUT THE INVENTION

The following will describe the invention in detail.

The term "lower" in the definition of the general formulae herein means a linear or branched carbon chain having 1 to 6 carbon atoms (hereinafter abbreviated as $C_{1-6}$) unless otherwise noted. Therefore, "lower alkyl" is $C_{1-6}$ alkyl, preferably linear alkyl such as a methyl, ethyl, n-propyl, or n-butyl group and branched alkyl such as an isopropyl, isobutyl, tert-butyl, or neopentyl group. Methyl, ethyl, n-propyl, and isopropyl groups are particularly preferred. "Lower alkylene" is $C_{2-6}$ alkylene, preferably linear alkylene such as an ethylene, trimethylene, or tetramethylene group and branched alkylene such as a propylene, ethylethylene, 1,2-dimethylethylene, or 1,1,2,2-tetramethylethylene group.

The linear or branched alkyl having 1 to 8 carbon atoms in $R^7$ is preferably an ethyl, n-propyl, isopropyl, n-butyl, isobutyl, isopentyl, or neopentyl group.

The "alkenyl" is a group having one or more double bonds in any position of "alkyl", preferably $C_{3-8}$ alkenyl, more preferably $C_{3-8}$ alkenyl having three or less branches, still preferably $C_{3-6}$ alkenyl having one double bond.

The "lower alkenylene" is a group having one or more double bonds in any position of $C_{3-6}$ alkylene, preferably propenylene, butenylene, pentenylene, hexenylene, or 1,3-butadienylene, more preferably $C_{2-4}$ alkenylene.

The linear or branched alkenyl having 3 to 8 carbon atoms in $R^7$ is preferably a propenyl, butenyl, butenyl, pentenyl, hexenyl, 1,3-butadienyl, isoprenyl, or 3,3-dimethylpropen-2-yl group.

The "halogen" represents F, Cl, Br, or I. Preferably, it is F or Cl. "Halogeno-lower alkyl" means $C_{1-6}$ alkyl substituted with one or more halogen, preferably $C_{1-6}$ alkyl substituted with one or more F, more preferably a trifluoromethyl group.

The "cycloalkyl" is a $C_{3-10}$ saturated hydrocarbon ring group and may have bridge. It is preferably a cyclopropyl, cyclobutyl, cyclopentyl, cyclohexyl, cycloheptyl, cyclooctyl, or adamantyl group, particularly preferably a cyclopentyl, cyclohexyl, or cycloheptyl group.

The cycloalkyl which may contain an oxygen atom includes a group wherein one of any carbon atoms of cycloalkyl is replaced by an oxygen atom in addition to the above cycloalkyl. The cycloalkyl which may contain an oxygen atom is preferably an oxiranyl, oxetanyl, tetrahydrofuranyl, or tetrahydropyranyl group.

The "monocyclic or bicyclic heterocyclic group" includes both of a "monocyclic heterocyclic group" and a "monocyclic or bicyclic heterocyclic group" which is a bicyclic group formed by fusion of the two "monocyclic heterocyclic groups" themselves or the "monocyclic heterocyclic group" with phenyl or cycloalkyl.

The "monocyclic heterocyclic group" is a monocyclic 3- to 8-membered, preferably 5- to 7-membered cyclic group having 1 to 4 heteroatoms selected from O, S, and N and includes "monocyclic hateroaryl" which is aromatic, "monocyclic saturated heterocyclic group" which is aliphatic and contains no unsaturated bond, and "monocyclic unsaturated heterocyclic group" which is aliphatic and partially contains an unsaturated bond. The "monocyclic heteroaryl" is preferably a pyridyl, pyrazinyl, pyrimidinyl, pyridazinyl, imidazolyl, pyrrolyl, triazolyl, tetrazolyl, thienyl, furyl, thiazolyl, pyrazolyl, isothiazolyl, oxazolyl, isoxazolyl, thiadiazolyl, and oxadiazolyl groups. The "monocyclic saturated heterocyclic group" or "monocyclic unsaturated heterocyclic group" is preferably pyrrolidinyl, piperidyl, piperazinyl, azepanyl, diazepanyl, oxetanyl, tetrahydrofuranyl, tetrahydropyranyl, tetrahydrothiopyranyl, 1,3-dioxolanyl, morpholinyl, or thiazolidinyl group.

The "bicyclic heterocyclic group" is preferably an indolyl, isoindolyl, indolinyl group, indazolyl, benzothiazolyl, benzoxazolyl, benzimidazolyl, quinolyl, isoquinolyl, tetrahydroquinolyl, tetrahydroisoquinolyl, quinazolyl, cinnolinyl, phthaladinyl, quinoxalinyl, octahydroindolinyl, or chromanyl group.

The "nitrogen-containing saturated heterocycle" represents 5- to 8-membered saturated or partially unsaturated monocyclic heterocycle (monocyclic nitrogen-containing saturated heterocycle) which contains one N atom and may further contain one heteroatom comprising N, S, and O or a ring wherein the monocyclic nitrogen-containing saturated heterocycle and a benzene ring are fused. Preferred are pyrrolidine, piperidine, piperazine, azepane, diazepane, azocane, morpholine, thiomorpholine, tetrahydropyridine, indoline, isoindoline, tetrahydroquinoline, tetrahydroisoquinoline, and dihydrobenzooxazine rings. More preferably, it is pyrrolidine, piperidine, homopiperidine, azepane, azocane, and morpholine rings.

In the above "nitrogen-containing saturated heterocycle", a ring atom, S may be oxidized to form an oxide or dioxide or N may be oxidized to form an oxide. Moreover, any carbon atom may be substituted with an oxo group.

Among the compound of the invention represented by the above general formula (I), a preferable embodiment is a compound represented by the following general formula (I⁴) or a salt thereof:

[Chem. 5]

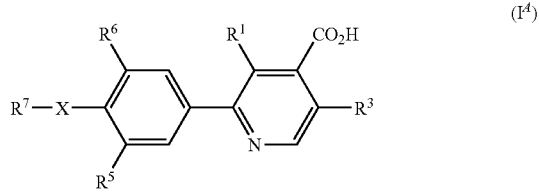

(I⁴)

wherein the symbols have the following meanings:
$R^1$: H or halogen,
$R^3$: the same or different from each other, H or lower alkyl,
$R^5$: —CN or halogeno-lower alkyl,
$R^6$: H or halogen,
X: —O—, —N($R^8$)—, or —S—,
$R^8$: H or lower alkyl
$R^7$: linear or branched alkyl having 1 to 8 carbon atoms,
linear or branched alkenyl having 3 to 8 carbon atoms,
—Y-(cycloalkyl which may contain an oxygen atom), —Y-phenyl,
or —Y-monocyclic heteroaryl,
where the linear or branched alkyl having 1 to 8 carbon atoms and linear or branched alkenyl having 3 to 8 carbon atoms may be substituted with one to three groups selected from the group consisting of —CN, —O-lower alkyl, —S-lower alkyl, and halogen, which may be the same or different from each other; the cycloalkyl which may contain an oxygen atom, phenyl, and monocyclic heteroaryl may be substituted with one to four groups selected from the group consisting of —CN, halogen, and lower alkyl, which may be the same or different from each other,
Y: bond, lower alkylene, lower alkenylene, or -(lower alkylene)-O—,
where, when X is a group represented by —N($R^8$)—, $R^8$ and $R^7$ are combined together with the adjacent nitrogen atom to form a nitrogen-containing saturated heterocycle and the nitrogen-containing saturated heterocycle may be substituted with one or two groups selected from the group consisting of lower alkyl, —O-lower alkyl, —CON(lower alkyl)$_2$, —CO$_2$-lower alkyl, halogen, phenyl, (cycloalkyl which may be substituted with lower alkyl), and —O-lower alkylene-cycloalkyl, which may be the same or different from each other.

The following show preferable embodiments of the compound of the invention represented by the general formula (I) and (I⁴):
[1] The compound wherein $R^1$ is H or F;
[2] More preferably, the compound according to the above [1], wherein $R^5$ is —CN or —NO$_2$, further preferably —CN;
[3] More preferably, the compound according to the above [2], wherein $R^6$ is H or halogen, further preferably H;
[4] More preferably, the compound according to the above [3], wherein X is —O— or —N($R^8$)—;
[5] More preferably, the compound of the following [5a] to [5c];
    [5a] the compound according to the above [4], wherein X is —O— and $R^7$ is a linear or branched alkyl group having 2 to 6 carbon atoms, further preferably, the compound according to the above [4], wherein X is —O— and $R^7$ is an ethyl, n-propyl, isopropyl, n-butyl, isobutyl, isopentyl, or neopentyl group;
    [5b] the compound according to the above [4], wherein X is —O— or —NH— and $R^7$ is a cycloalkyl group having 3 to 6 carbon atoms which may contain an oxygen atom, further preferably, the compound according to the above [4], wherein X is —O— or —NH— and $R^7$ is a cyclopentyl, cyclohexyl, cycloheptyl, tetrahydrofuranyl, or tetrahydropyranyl group;
    [5c] the compound according to the above [4], wherein X is —N($R^8$)— and $R^8$ and $R^7$ are combined together with the adjacent nitrogen atom to form a nitrogen-containing saturated heterocycle which may be substituted with lower alkyl, further preferably the compound wherein the nitrogen-containing saturated heterocycle is a pyrrolidine, piperidine, homopiperidine, azepane, azocane, or morpholine ring.

Particularly preferable compounds are at least one compound selected from the following group: 2-(3-cyano-4-isobutoxyphenyl)isonicotinic acid, 2-(3-cyano-4-piperidin-1-ylphenyl)isonicotinic acid, 2-{3-cyano-4-[(3,3,5,5-tetramethylcyclohexyl)oxy]phenyl}isonicotinic acid, 2-(4-azepan-1-yl-3-cyanophenyl)isonicotinic acid, 2-[3-cyano-4-(isobutylthio)phenyl]isonicotinic acid, 2-[3-cyano-4-(4-methylpiperidin-1-yl)phenyl]isonicotinic acid, 2-[3-cyano-4-(4-fluoropiperidin-1-yl)phenyl]isonicotinic acid, 2-[3-cyano-4-(isobutylamino)phenyl]isonicotinic acid, 2-{3-cyano-4-[hexyl(methyl)amino]phenyl}isonicotinic acid, 2-[3-cyano-4-(cyclohexylamino)phenyl]isonicotinic acid, 2-[3-cyano-4-(cycloheptylamino)phenyl]isonicotinic acid, and 2-(3-cyano-5-fluoro-4-isobutoxyphenyl)isonicotinic acid.

Depending on the kinds of substituents, the compounds of the invention have tautomers and optical isomers, and the invention includes mixtures and isolated forms of these isomers.

Furthermore, a "pharmaceutically acceptable prodrug" of the compound represented by the general formula (I) is also included in the invention. The "pharmaceutically acceptable prodrug" is a compound which releases the compound (I) of the invention by generation of a certain group such as CO$_2$H, NH$_2$, and OH through solvolysis or under a physiological condition. Examples of the group which form the prodrug include those which are described in Prog. Med., 5, 2157-2161 (1985) and "Iyakuhin no Kaihatsu" (Hirokawa Publishing Co., 1990), Vol. 7, Bunshi Sekkei 163-198. Incidentally, among the compounds represented by the general formula (I), the compound wherein $R^2$ is —CO$_2$-lower alkyl is a compound which itself functions as a prodrug.

The salts of the compound (I) of the invention are pharmaceutically acceptable salts, and their specific examples include acid addition salts with inorganic acids such as hydrochloric acid, hydrobromic acid, hydroiodic acid, sulfuric acid, nitric acid, and phosphoric acid and organic acids such as formic acid, acetic acid, propionic acid, oxalic acid, malonic acid, succinic acid, fumaric acid, maleic acid, lactic acid, malic acid, tartaric acid, citric acid, methanesulfonic acid, ethanesulfonic acid, aspartic acid, and glutamic acid. In addition, depending on the kind of the substituent, salts with bases may be formed in some cases and examples thereof include salts with inorganic bases including metals such as sodium, potassium, magnesium, calcium, and aluminum and organic bases such as methylamine, ethylamine, ethanolamine, lysine, and ornithine, and ammonium salts.

Furthermore, the compounds (I) of the invention and salts thereof include various hydrates, solvates, and polymorphic substances thereof.

(Production Method)

The compound of the invention can be produced by applying various known synthetic methods making use of the characteristics based on its basic skeleton or the kind of substituent. In that case, depending on the kind of functional group, it is sometimes effective from the production technical point of view to protect the functional group with an appropriate protective group or replace the group by a group, which can be easily converted into the functional group, at the starting material or intermediate stage. Such functional groups are, for example, an amino group, a hydroxy group, a carboxyl group, and the like and examples of protective groups thereof include protective groups described in "Protective Groups in Organic Synthesis (3rd Ed.)" written by T. W. Greene and P. G. M. Wuts, which may be suitably used in response to the reaction conditions. In such a method, after the protective group is introduced and then a reaction is carried out, the desired compound can be obtained by appropriate removing the protecting group or converting the group into the desired group.

Moreover, as in the above protective group, the prodrug of the compounds of the invention or salt thereof can be produced by introducing a specific group or carrying out a reaction using the obtained compound (I) at the starting material or intermediate stage. The reaction can be carried out by applying a method such as usual esterification, amidation, or the like known by those skilled in the art.

First Production Method

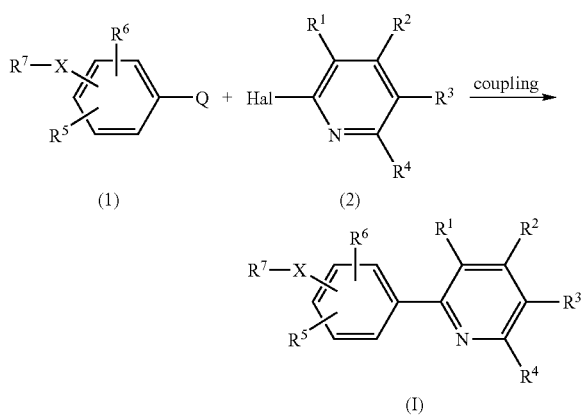

[Chem. 6]

wherein Q represents —B(OH)$_2$ or —B(OR$^{12}$)OR$^{13}$ and Hal represents halogen, where R$^{12}$ and R$^{13}$ are the same or different from each other and each represents lower alkyl or R$^{12}$ and R$^{13}$ are combined to represent lower alkylene; the same shall apply hereinafter.

The present production method is a method of producing the compound (I) of the invention by coupling, the compound (1) and the compound (2).

The halogen represented by Hal is preferably chlorine, bromine, iodine, or the like. For the reaction, compound (1) and compound (2) are used in an equimolar amount or in an excessive amount for either of the compounds and the mixture is stirred in a solvent inert under the reaction conditions, in the presence of a base and a palladium catalyst, at room temperature to reflux, generally for 0.1 hours to 5 days. The solvent is not particularly limited but examples thereof include aromatic hydrocarbons such as benzene, toluene, and xylene; ethers such as diethyl ether, tetrahydrofuran (THF), 1,4-dioxane, 1,2-dimethoxyethane, and 1,2-diethoxyethane; halogenated hydrocarbons such as dichloromethane, 1,2-dichloroethane, and chloroform; alcohols such as methanol, ethanol, 2-propanol, and butanol; N,N-dimethylformamide (DMF), N-methylpyrrolidone (NMP), dimethyl sulfoxide (DMSO), water, mixed solvents thereof, and the like. As the base, inorganic bases such as sodium carbonate, potassium carbonate, sodium hydroxide, potassium hydroxide, sodium ethoxide, and sodium methoxide are preferred. Moreover, bases such as potassium fluoride and cesium fluoride can be used but, in this case, it is preferable to carry out the reaction in an aprotic solvent. As the palladium catalyst, tetrakis(triphenylphosphine)palladium, dichlorobis(triphenylphosphine) palladium, 1,1'-bis(diphenylphosphino)ferrocene palladium chloride, and the like are preferred.

Second Production Method

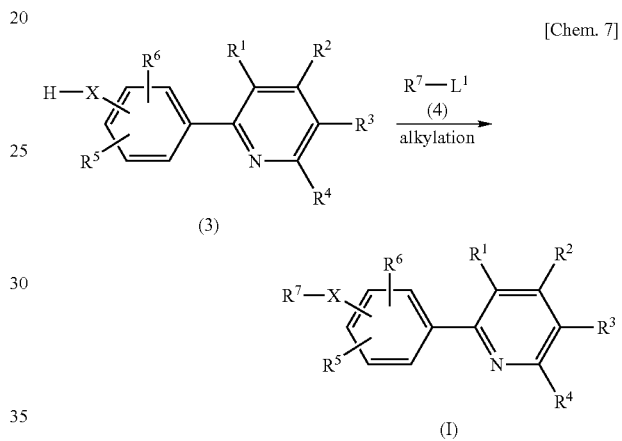

[Chem. 7]

wherein L$^1$ represents a leaving group or OH; the same shall apply hereinafter.

The present production method is a method of producing the compound (I) of the invention by subjecting a compound represented by the general formula (3) to an alkylation reaction.

The leaving group represented by L$^1$ includes halogen, methanesulfonyloxy, p-toluenesulfonyloxy, trifluoromethanesulfonyloxy, or the like.

In the case that L$^1$ is a leaving group, the production method is carried out by reacting the compounds (3) with the alkylating agent (4) in a solvent inert to the reaction at room temperature to reflux for usually from 0.1 hour to 5 days using them in an equimolar amount or the alkylating agent in excess. The solvent is not particularly limited but examples thereof include aromatic hydrocarbons, ethers, halogenated hydrocarbons, DMF, NMP, DMSO, mixed solvents thereof, and the like, as mentioned above. The reaction is sometimes preferably carried out in the presence of a base or a phase transfer catalyst. In this case, the base includes organic bases such as triethylamine, diisopropylethylamine (DIPEA), and 1,8-diazabicyclo[5.4.0]-7-undecene (DBU) and inorganic bases such as sodium carbonate, potassium carbonate, cesium carbonate, and sodium hydride. Moreover, the phase transfer catalyst includes tetra-n-butylammonium chloride, tetra-n-butylammonium bromide, 18-crown-6, and the like.

Moreover, in the case that L$^1$ is OH and X is O, the alkylation is carried out by using the compounds (3) with the alkylating agent (4) in an equimolar amount or the alkylating agent in excess and treating them with an azodicarbocylic acid derivative such as ethyl azodicarboxylate or 1,1'-(azodicarbonyl)dipiperidine and a phosphorus compound such as triphenylphosphine or tributylphosphine. Specific reaction conditions and reaction reagents are described in detail in "Organic Reactions 42, 335-656 (1992)" and "Journal of Synthetic Organic Chemistry, Japan 53, 631-641 (1997)" and the reaction can be carried out according to the method or with reference to the method.

Third Production Method

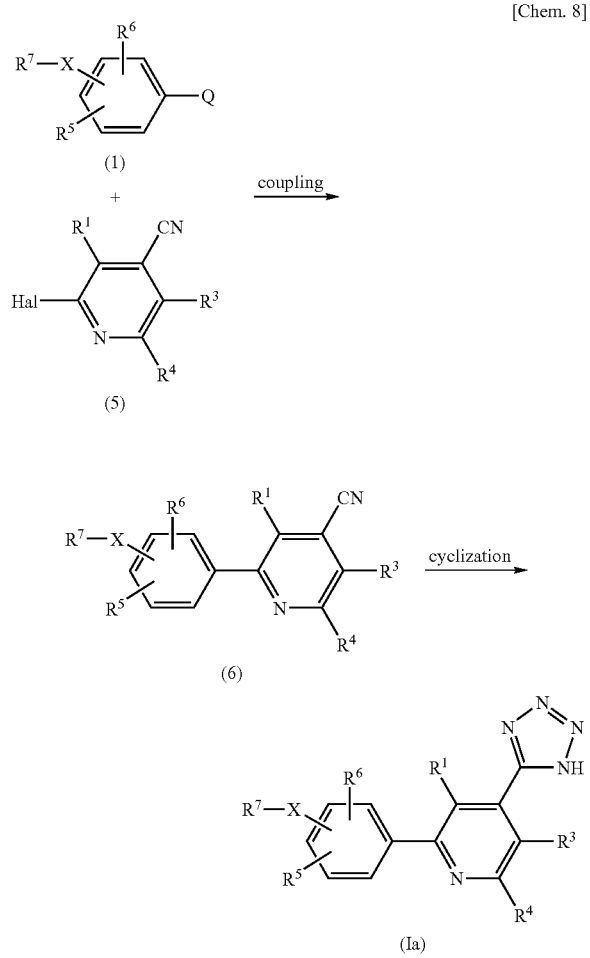

The present production method is a method of producing the compound (Ia) of the invention by subjecting the compound (1) and the compound (5) to a coupling reaction and subsequently tetrazole ring-cyclization of the product.

In the coupling reaction, the same conditions as in the above First Production Method can be applied. The tetrazole ring-cyclization is carried out by treating the compound (6) with sodium azide in a solvent inert to the reaction, such as an aromatic hydrocarbon, an ether, a halogenated hydrocarbon, DMF, or water or in a mixed solvent thereof in the presence or absence of an acid at 0° C. to 250° C. As the acid, a protonic acid such as hydrogen chloride and a salt thereof with an organic acid such as triethylamine, and a Lewis acid such as zinc chloride are preferred.

Fourth Production Method

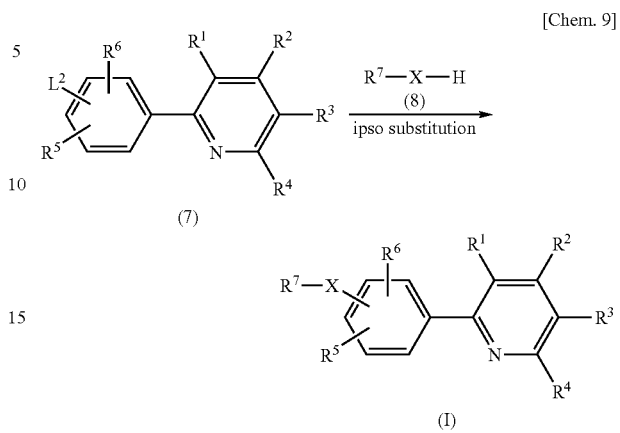

wherein $L^2$ represents a leaving group; the same shall apply hereinafter.

The present production method is a method of producing the compound (I) of the invention by subjecting the compound (7) and the compound (8) to an ipso substitution reaction.

The leaving group represented by $L^2$ includes halogen, methanesulfonyloxy, p-toluenesulfonyloxy, trifluoromethanesulfonyloxy, and the like. In the reaction, the same conditions as in the above Second Production Method can be applied.

Incidentally, in the reactions described in First Production Method, Second Production Method, and Fourth Production Method, in the case of the compounds having —$CO_2H$ or tetrazolyl group as $R^1$, the group is preferably protected with a protective group. As the protective group and conditions for protection and deprotection, the methods described in "Protective Groups in Organic Synthesis (3rd Ed., 1999)" in the case of —$CO_2H$ group and the methods described in "J. Med. Chem. 34, 2525-2547, (1991)" and "Chem. Pharm. Bull. 46, 973-981 (1998)" in the case of the tetrazolyl group can be referred to.

Other Production Methods

The compounds of the invention having various functional groups can be produced by methods obvious to those skilled in the art or known production methods, or by applying modified methods thereof. For example, desired compounds of the invention can be produced by further subjecting the compounds of the invention obtained by the above production methods to transforming reactions of substituents. Representative reactions are shown in the following.

(1) Amidation and Esterification

Among the compounds (I) of the invention, a compound having an amide group or a compound having an ester group can be produced by using a compound having a hydroxyl group or an amino group as a starting material and reacting it with a carboxylic acid or a reactive derivative thereof. The reaction can be carried out by referring to the methods described, for example, in "JIKKEN KAGAKU KOZA (Courses in Experimental Chemistry) (4th Ed.)" edited by The Chemical Society of Japan, vol. 22 (1992) (Maruzen) and the like.

(2) Oxidation

Among the compounds (I) of the invention, a compound having an S-oxide can be produced by an oxidation reaction of the sulfur atom. The reaction can be carried out by the methods described, for example, in "JIKKEN KAGAKU KOZA (Courses in Experimental Chemistry) (4th Ed.)" edited by The Chemical Society of Japan, vol. 23 (1991) (Maruzen) and the like.

(3) Alkylation

Among the compounds (I) of the invention, a compound having a lower alkoxy group or a lower alkylamino group can be produced by subjecting a compound having a hydroxyl group or an amino group to an alkylation reaction. The reaction can be carried out under the same conditions as in Second Production Method.

Synthesis of Starting Materials

[Chem. 10]

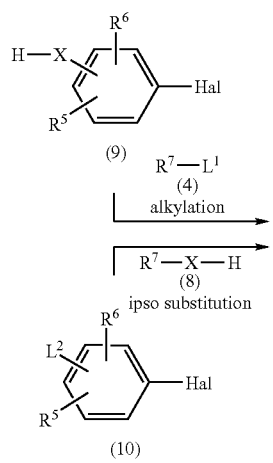

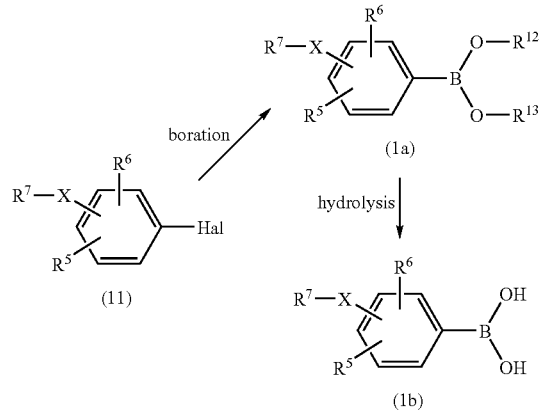

The starting materials (1a) and (1b) can be produced by the above reaction pathway.

In the above reaction pathway, to the alkylation reaction, the same conditions as in the above Second Production Method can be applied.

Moreover, in the ipso substitution reaction, the reaction may be carried out using the compound (10) and the compound (8) under the same conditions as in the alkylation in the case that $L^1$ is a leaving group described in the above Second Production Method.

The boration can be carried out according to the methods described in "Chem Rev. 95, 2547-2483 (1995)", "J. Org. Chem. 67, 5394-5397 (2002)", "J. Org. Chem. 65, 164-168 (2000)", or "J. Org. Chem. 60, 7508-7510 (1995)".

The hydrolysis can be carried out according to the methods described in "Chem Rev. 95, 2547-2483 (1995)" or "J. Org. Chem. 67, 5394-5397 (2002)".

[Chem. 11]

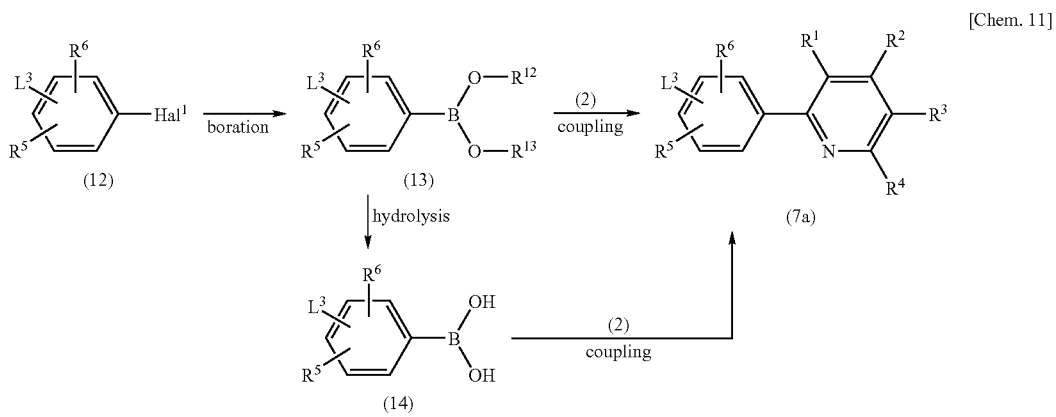

wherein $L^3$ represents F or Cl, and Hall represents Br or I; the same shall apply hereinafter.

The starting material (7a) can be produced by the above reaction pathway.

In the above reaction pathway, to the boration and hydrolysis, the same conditions as in the case of the compounds (1a) and (1b) of the above formulae can be applied. Moreover, to the coupling reaction, the same conditions as in the above First Production Method can be applied.

Among the starting materials (7), the compounds wherein $L^2$ is a methanesulfonyloxy, p-toluenesulfonyloxy, or trifluoromethanesulfonyloxy group can be produced from the compound having a hydroxyl group using a usual manner for sulfonyl ester formation.

The compound (I) thus produced is isolated and purified as its free form or a salt thereof, the salt being produced by carrying out a usual salt formation treatment. The isolation and purification are carried out by employing usually used chemical techniques such as extraction, concentration, evaporation, crystallization, filtration, recrystallization and various types of chromatography.

Various isomers can be isolated in the usual way making use of the difference in physicochemical properties between corresponding isomers. For example, optical isomers can be separated from each other by a general optical resolution method such as fractional crystallization after conversion of a racemic compound into a diastereomer salt with an optically active organic acid (tartaric acid or the like) or chromatography using a chiral packing material. Also, an optical isomer can be produced starting from an appropriate optically active starting compound. In this connection, a mixture of diastereomers can be separated by fractional crystalization or chromatography.

(Test Method)

The advantages of the compound of the invention are confirmed by the following pharmacological tests.

1. Xanthine Oxidase-Inhibitory Activity (1) Preparation of Test Compound

A test compound was dissolved in DMSO (manufactured by Nakarai) so as to be a concentration of 10 mM and then used after the concentration was adjusted to an aimed one at use.

(2) Measuring Method

The evaluation of xanthine oxidase-inhibitory activity of the compound of the invention was carried out using a method described in a document (Free Radic. Biol. Med. 6, 607-615, 1992) with partial modification. Namely, xanthine oxidase (derived from butter milk, manufactured by Sigma) was adjusted to 0.03 units/ml using a 50 mM phosphate buffer and was added to a 96-well plate in an amount of 50 μl/well. Each test compound diluted so as to be a final concentration was added thereto in an amount of 2 μl/well, followed by treatment at room temperature for 20 minutes. Pterin (manufactured by Sigma) was added thereto so as to be a final concentration of 5 μM, followed by reaction at room temperature for 10 minutes. Measurement was performed using a microplate reader saphire (manufactured by Tecan) under conditions of excitation at 345 nm and emission at 390 nm (pterin was oxidized by xanthine oxidase into isoxanthopterin, which emitted a light under the conditions).

The concentration of the test compound at which 50% inhibition was observed ($IC_{50}$ value) was calculated, the emissions of isoxanthopterin under conditions of the presence or absence of xanthine oxidase being 0% inhibition and 100% inhibition, respectively.

The compounds of the invention had good xanthine oxidase-inhibitory activity. The $IC_{50}$ values of representative compounds of Examples are shown in the following Table 1.

TABLE 1

| Example | $IC_{50}$ (nM) | Example | $IC_{50}$ (nM) | Example | $IC_{50}$ (nM) | Example | $IC_{50}$ (nM) |
|---|---|---|---|---|---|---|---|
| 1 | 3.6 | 3 | 5.0 | 4 | 1.2 | 7 | 2.5 |
| 9 | 2.6 | 13 | 10 | 14 | 4.1 | 21 | 10 |
| 30 | 4.2 | 33 | 7.3 | 44 | 4.3 | 45 | 1.3 |
| 49 | 2.8 | 57 | 3.1 | 63 | 1.1 | 67 | 2.2 |
| 72 | 3.1 | 75 | 3.2 | 77 | 4.0 | 79 | 5.8 |

From the above test, it was confirmed that the compounds of the invention had potent xanthine oxidase-inhibitory activity.

2. Serum Uric Acid-Lowering Action

A test compound was orally administered compulsorily to ICR mice using an oral sonde. After 2 hours, 6 hours, and, depending on the compound, further 24 hours from the administration, blood was collected from an abdominal aorta and then serum was separated in a usual manner. Serum uric acid was measured on an absorptiometer (SPECTRA MAX 190, manufactured by Molecular Device) by an uricase method using a uric acid-measuring kit (Uric Acid C-TestWako: Wako Pure Chemical Industries, Ltd.) and a uric acid-lowering ratio was determined according to the following equation.

Uric acid-lowering ratio (%)=(Uric acid level of control animal−Uric acid level of test compound-administered animal)×100/Uric acid level of control animal In the test, an excellent serum uric acid-lowering action of the compounds of the invention was confirmed. For example, the compounds of Examples 4, 35, and 44 showed a uric acid-lowering ratio of 80% or more after 2 hours from the oral administration thereof in an amount of 1 mg/kg. Moreover, the compounds of the invention exhibited a highly long-acting action and, for example, 50% or more of uric acid-lowering ratio after 24 hours from the administration remained in the compounds of Examples 4, 6, 7, 44, 50, 51, 54, 56, 57, 58, 60, 62, and 84.

From the above results, it was revealed that the compounds of the invention had a strong and long-acting serum uric acid-lowering action.

3. Acetic Acid-Induced Enteritis-Suppressing Action

One ml of 3% acetic acid was administered into the rectum of a Wistar rat of 2 days of fasting. A group wherein 1 ml of physiological saline had been administered instead of acetic acid was separately prepared as a normal group. Thereafter, to the 3% acetic acid-administered group, a test compound or 0.5% methyl cellulose (control group) was orally administered once a day and dissection was performed on each administered group on fourth day. A part of the large intestine 2 to 7 cm from the anus side was cut out and incised. After feces were removed by means of tweezers, the part was washed and a score of morbid conditions was evaluated and tissue weight was measured. The score of morbid conditions and a tissue weight increase-suppressing ratio were calculated by the following methods. Score of morbid conditions: feces, general conditions, adhesion, perforation, cell death, ulcer, edema, and megacolon each was evaluated and point-rated with dividing into four stages.

Tissue weight increase-suppressing ratio (%)=100−
{(Tissue weight of test compound-administered
group−Tissue weight of normal group)/(Tissue
weight of control group−Tissue weight of normal
group)×100}

As a result, as compared with the normal group wherein physiological saline had been administered into the rectum, deterioration of the score of morbid conditions and remarkable erosion and resulting intestinal tissue weight increase were observed in the 3% acetic acid-administered group. On the other hand, when the test compound-administered group was compared with the control group, significant improvement in the score of morbid conditions and suppression of intestinal tissue weight increase were observed in the test compound-administered group in comparison with the control group.

For example, the compounds of Examples 4 and 45 suppressed 70% or more of the intestinal tissue weight increase when administered in an amount of 10 mg/kg.

From the above results, the effectiveness of the compound of the invention on ulcerative colitis was shown.

4. Trinitrobenzenesulfonic Acid-Induced Enteritis-Inhibitory Action

The effectiveness of the compound of the invention on an enteritis model can be also evaluated by a model using trinitrobenzenesulfonic acid (TNBS) as an inducing agent instead of acetic acid (Cell. Mol. Biol, 38, 189-199, 1992). Thus, referring to the method described in the report, the enteritis-suppressing action of the compound of the invention was evaluated.

Namely, TNBS or physiological saline as a normal group was administered into the rectum of male Wistar rats of 200 to 250 g. Thereafter, a test compound or 0.5% methyl cellulose (control group) was orally administered once a day and dissection was performed on each administered group on 21st day. A part of the large intestine 2 to 7 cm from the anus side was cut out and incised. After feces were removed by means of tweezers, the part was washed and a score of morbid conditions was evaluated and tissue weight was measured. The score of morbid conditions and a tissue weight increase-suppressing ratio were calculated as in the evaluation method of the above acetic acid-induced enteritis-suppressing action.

As a result, as compared with the normal group wherein physiological saline had been administered into the rectum, deterioration of the score of morbid conditions and remarkable erosion and resulting intestinal tissue weight increase were observed in the TNBS-administered group. On the other hand, when the test compound-administered group was compared with the control group, significant improvement in the score of morbid conditions and suppression of intestinal tissue weight increase were observed in the test compound-administered group in comparison with the control group.

For example, the compound of Example 4 suppressed 70% or more of the intestinal tissue weight increase when administered in an amount of 3 mg/kg.

From the above results, the effectiveness of the compound of the invention on ulcerative colitis was shown.

As above, from the test results of 3 and 4, it was revealed that the compounds of the invention had a strong antiinflammatory action.

5. Pyrimidine Synthetic Pathway-Inhibitory Action

Allopurinol which is an existing hyperuricemia therapeutic drug is known to cause renal dysfunction as an undesirable action. As mentioned previously, since allopurinol has a nucleic acid-like structure, as one cause thereof, it is presumed that it inhibits pyrimidine synthetic pathway. In recent studies on xanthine oxidase inhibitors, there have been desired compounds which do not influence pyrimidine synthetic pathway. For example, it has been reported that the comparative compound 3 has reduced BUN (Blood Urea Nitrogen) concentration-increasing action, which is an index of renal dysfunction, as compared with allopurinol (Research Communications in Molecular Pathology and Pharmacology, 104(3), 293-305, (1999)). Thus, according to the method described in the document, the influence of the compounds of the invention on a BUN level was confirmed.

As a result, it was found that the influence of the compounds of the invention on the BUN level was small. For example, the compounds of Examples 4 and 45 exhibited no inhibitory action at an oral administration of 30 mg/kg.

From the above results, since the compounds of the invention do not inhibit the pyrimidine synthetic pathway, there was revealed an advantage that the compounds do not exhibit adverse effects based thereon.

6. AKR1C3 Inhibitory Action

AKR1C3 known as a molecule belonging to aldo-keto reductase is known as a multifunctional enzyme (Jikken Igaku 23, 90-97, 2005). There is expected the application of a compound inhibiting AKR1C3 to various morbid conditions including inflammatory diseases (Mol. Pharmacol 67, 60-68, 2005) (Current Pharmaceutical Design 10, 3505-3524, 2004) (J. Biol. Chem 273, 1855-1888, 1998). As a result of testing the presence of AKR1C3 (17βHSD5) inhibitory activity on the compounds of the invention according to the method described in DELFIA (registered trademark) Testosterone Reagents R050-201 (manufactured by Perkin Elmer), it was found that the compounds surprisingly have inhibitory activity against the enzyme. For example, the compound of Example 4 showed an $IC_{50}$ value of 1 μM or less.

From the above results, the compound of the invention was suggested to be compounds having an inflammatory action independently of xanthine oxidase inhibition. Therefore, the compound of the invention is expected as an antiinflammatory drug having a high efficacy.

7. Diabetic Retinopathy Model

The efficiency of the compound of the invention on diabetic retinopathy was tested by the method described in European Journal of Pharmacology 458 (2003) 283-289 (except that the animal used in the experiment was male Wistar rat, 10 weeks old).

Streptozotocin (STZ) was administered to the animals to be tested and increase in blood sugar level was confirmed after 24 hours. Thereafter, the animals were divided into a 0.5% methyl cellulose-administered group (control group) and 30 mg/kg test compound-administered group and oral administration was performed once a day for 7 days.

As a result, as compared with the normal rats, a remarkable increase of VEGF mRNA in the vitreous body was observed in the control group. On the other hand, in the group to which the compound of the invention had been administered, suppression of increase of VEGF mRNA was observed as compared with the control group. For example, the Example compound 4 exhibited a significant suppressing action. These results showed the efficiency of the compound of the invention on diabetic retinopathy.

From the above tests, the following were confirmed: (1) the compound of the invention has a xanthine oxidase-inhibitory action and excellent uric acid-lowering action and antiinflammatory action based thereon; (2) the compound of the invention has little influence on the BUN level and hence can avoid adverse effects such as renal dysfunction based on the inhibition of pyrimidine metabolic pathway; (3) the compound of the invention inhibits not only xanthine oxidase but also AKR1C3 and has an excellent profile as an antiinflammatory drug; and (4) the compound of the invention is also effective in diabetic complications such as diabetic retinopathy. Incidentally, the compound of the invention is superior to uric acid-excreting agents in view of the fact that the compound of the invention is also effective in hyperuricemia patients having decreased renal function.

The pharmaceutical composition containing the compound (I) of the invention or a salt thereof as an active ingredient may be prepared using a carrier, an excipient, and other additives generally used in formulation.

The administration may be in any form of oral administration by means of tablets, pills, capsules, granules, powders, or liquids or parenteral administration by means of injections such as intravenous injections or intramuscular injections, suppositories, subcutaneous preparations, transnasal preparations, or inhalations. The dose may be suitably determined, depending on individual cases in consideration of the symptom, the age and the sex of the patients of administration targets, but is, in general, from about 0.001 to 100 mg/kg per adult per day in the case of oral administration and this may be administered all at a time or may be divided into a few portions for administration in 2 to 4 times. In the case of intravenous administration, the dose is, in general, from about 0.0001 to 10 mg/kg per adult per time and administration was performed once a day or plurality of times per day. In the case of inhalation, the dose is, in general, from about 0.0001 to 1 mg/kg per adult per time and administration was performed once a day or plurality of times per day.

As the solid composition for oral administration in accordance with the invention, tablets, powders, granules, and the like are used. In such a solid composition, one or more active substances are mixed with at least one inactive excipient, for example, lactose, mannitol, glucose, hydroxypropyl cellulose, microcrystalline cellulose, starch, polyvinylpyrrolidone, magnesium metasilicate aluminate, or the like. According to usual methods, the composition may contain inactive additives, for example, a lubricant such as magnesium stearate, a disintegrator such as sodium carboxymethylstarch, and a solubilizing agent. If necessary, the tablets or pills may be coated with sugar coating agents or gastrosoluble or enterosoluble coating agents.

The liquid composition for oral administration includes pharmaceutically acceptable emulsions, solutions, suspensions, syrups, and elixirs, and the like and contains inactive solvents generally used, for example, purified water and ethanol. The composition may contain an auxiliary agent such as a solubilizer, a wetting agent, and a suspending agent, a sweetener, a flavoring agent, an aromatic agent, and a preservative in addition to the inactive solvents.

The injections for parenteral administration encompass aseptic, aqueous or non-aqueous solutions, suspensions, and emulsions. The solvents for aqueous solutions include, for example, distilled water for injections and physiological saline. The non-aqueous solvents include, for example, propylene glycol, polyethylene glycol, vegetable oils such as olive oil, alcohols such as ethanol, polysorbate 80 (name in Pharmacopeia), and the like. Such a composition may further contain an isotonic agent, a preservative, a wetting agent, an emulsifier, a dispersant, a stabilizer, and a solubilizing agent. These may be sterilized, for example, by filtration through a bacteria-retaining filter, blending with germicides, or irradiation. These may be also prepared into aseptic solid compositions and the compositions may be used, after dissolution in aseptic water or aseptic solvents for injections prior to use.

The transmucomembranous preparations such as inhalations and transnasal preparations are used in the form of solid, liquid, or semi-solid, and may be produced in accordance with hitherto known methods. For example, an excipient such as lactose or starch and further a pH regulating agent, an antiseptic, a surfactant, a lubricant, a stabilizer, and a thickening agent may be optionally added thereto. For the administration, an appropriate device for inhalation or blowing can be used. For example, using a known device such as a metered dose-inhaling device or a nebulizer, the compound may be administered solely or as a powder of formulated mixture, or as a solution or suspension in combination with a pharmaceutically acceptable carrier. A dry powder-inhaling device or the like may be a device for single use or a device for several uses, where a dry power or a capsule containing a power can be utilized. Alternatively, it may be in the form of a pressurized aerosol spray wherein an appropriate propellant, for example, a suitable gas such as chlorofluoroalkane, hydrofluoroalkane or carbon dioxide is employed.

In the production of suppositories, a low-melting wax, for example, a mixture of fatty acid glycerides or cocoa butter was melted, an active ingredient was added thereto, and the whole was homogeneously dispersed by stirring. Thereafter, the melt was poured into a suitable mold and solidified under cooling. The liquid preparations include solutions, suspensions, supported enemas, and emulsions, for example, water or aqueous propylene glycol solutions.

EXAMPLES

The following will explain the production methods of the compound (I) of the invention in further detail with reference to Examples. The invention is not limited to the invention of the compounds described in the following Examples. Also, production methods of starting materials are shown as Referential Examples.

The following abbreviations are used in Referential Examples, Examples, and the following Tables. Ex: Example No.; REx: Referential Example No.; Dat: physicochemical data (F: FAB-MS (M+H)$^+$, FN: FAB-MS (M−H)$^-$, ES: ESI-MS (M+H)$^+$, EI: EI-MS (M)$^+$, APN: API-ES-MS (M−H)$^-$, [Compound where (Na) is indicated after the above Mass spectroscopic measured value represents one observed as Na salt and compound where (G-2W) is indicated thereafter represents one observed as glycerin adduct di-dehydrate]; NMR: δ ppm of characteristic peaks in $^1$H-NMR in DMSO-d$_6$, NMRC: δ ppm of characteristic peaks in $^1$H-NMR in CDCl$_3$; Str: structural formula; Syn: Production method (each numeral indicates Example No., at which the compound was similarly produced); Sal: salt (compound not indicated represents a free compound); Me: methyl; Et: ethyl; nPr: n-propyl; iPr: isopropyl; nBu: n-butyl; iBu: isobutyl; tBu: tert-butyl; cBu: cyclobutyl; nPen: n-pentyl; iPen: isopentyl; cPen: cyclopentyl; nHex: n-hexyl; cHex: cyclohexyl; cHep: cycloheptyl; cOct: cyclooctyl; Bn: benzyl; Ph: phenyl; 2Py: 2-pyridyl, and 3Py: 3-pyridyl.

Referential Example 1

5-Bromo-2-hydroxybenzonitrile, isobutyl bromide, and potassium carbonate were heated at 80° C. in DMF in the presence of tetra-n-butylammonium bromide to obtain 5-bromo-2-isobutoxybenzonitrile. F: 254, 256.

Referential Example 2

After 2,2-dimethyl-1-propanol and sodium hydride were stirred at 0° C. in DMF, 5-bromo-2-fluorobenzonitrile was added thereto, followed by reaction at room temperature to obtain 5-bromo-2-(2,2-dimethylpropoxy)benzonitrile. NMRC: 3.67 (2H, s), 6.83 (1H, d), 7.64 (1H, d).

Referential Example 3

5-Bromo-2-fluorobenzonitrile and piperidine were heated at 80° C. in DMSO in the presence of cesium carbonate to obtain 5-bromo-2-piperidin-1-ylbenzonitrile. F: 265.

Referential Example 4

5-Bromo-2-isobutoxybenzonitrile and triisopropylborate were dissolved in a mixed solvent of THF and toluene and an n-butyllithium-hexane solution was added dropwise to the solution at a temperature below −60° C. After the temperature was elevated to −20° C., 1M hydrochloric acid was added, followed by stirring at room temperature to obtain (3-cyano-4-isobutoxyphenyl)boronic acid. F: 220.

Referential Example 5

Methyl 2-[4(benzyloxy)-3-cyanophenyl]isonicotinate and pentamethylbenzene were stirred at room temperature in trifluoromethanesulfonic acid to obtain methyl 2-(3-cyano-4-hydroxyphenyl)isonicotinate. F: 255.

Referential Example 6

Methyl 3-fluoroisonicotinate was oxidized with 3-chloroperbenzoic acid, followed by heating in the presence of phosphoryl chloride. The product was separated by silica gel column chromatography to obtain methyl 2-chloro-5-fluoroisonicotinate fluoroisonicotinate (EI: 189) and methyl 2-chloro-3-fluoroisonicotinate (EI: 189).

Referential Example 7

Methyl 2-(3-cyano-4-hydroxyphenyl)isonicotinate and N-chlorosuccinimide were stirred at room temperature in acetonitrile to obtain methyl 2-(3-chloro-5-cyano-4-hydroxyphenyl)isonicotinate. ES: 289.

Referential Example 8

Methyl 2-(3-cyano-4-hydroxyphenyl)isonicotinate and N-bromosuccinimide were stirred at room temperature in acetonitrile to obtain methyl 2-(3-bromo-5-cyano-4-hydroxyphenyl)isonicotinate. FN: 333.

Referential Example 9

Sodium hydride was added to a DMF solution of 2,3-difluorobenzonitrile and 2-(methylsulfonyl)ethanol, followed by stirring at room temperature to obtain 3-fluoro-2-hydroxybenzonitrile. FN: 136.
3-Fluoro-2-hydroxybenzonitrile and N-bromosuccinimide were stirred at room temperature in acetonitrile to obtain 5-bromo-3-fluoro-2-hydroxybenzonitrile. EI: 215, 217.

Referential Example 10

(3-Cyano-4-benzyloxy-5-fluorophenyl)boronic acid and methyl 2-chloroisonicotinate were dissolved in a mixed solution of toluene and a 2M aqueous sodium carbonate solution, followed by heating under reflux for 3 hours in the presence of tetrakis(triphenylphosphine)palladium to obtain methyl 2-(3-cyano-4-benzyloxy-5-fluorophenyl)isonicotinate. F: 363.

Methyl 2-(3-cyano-4-benzyloxy-5-fluorophenyl)isonicotinate is stirred at room temperature in methanol-THF (1:1) under a hydrogen atmosphere at normal pressure in the presence of palladium-carbon to obtain methyl 2-(3-cyano-5-fluoro-4-hydroxyphenyl)isonicotinate. FN: 271.

Referential Example 11

Methyl 2-(3-cyano-4-hydroxyphenyl)isonicotinate and trifluoromethanesulfonic anhydride were reacted at 0° C. in dichloromethane in the presence of diisopropylethylamine to obtain methyl 2-(3-cyano-4-([(trifluoromethyl)sulfonyl]oxy)phenyl)isonicotinate. F: 387.

Referential Example 12

Cesium fluoride and tetrakis(triphenylphosphine)-palladium were added to a 1,2-dimethoxyethane solution of (3-cyano-4-fluorophenyl)boronic acid and methyl 2-chloroisonicotinate, followed by reaction under heating to reflux to obtain methyl 2-(3-cyano-4-fluorophenyl)isonicotinate. F: 257.

Referential Examples 13 to 35

The compounds of Referential Examples 13 to 16 were produced in a similar manner to the method of Referential Example 1, the compounds of Referential Examples 17 to 21 were produced in a similar manner to the method of Referential Example 2, the compound of Referential Example 22 was produced in a similar manner to the method of Referential Example 3, and the compounds of Referential Examples 23 to 35 were produced in a similar manner to the method of Referential Example 4, using corresponding starting materials. The structure and physicochemical data of the compounds of Referential Examples 13 to 35 are shown in the following Table 2.

Example 1

(1) In a mixed solution of 50 ml of toluene and 30 ml of a 2M aqueous sodium carbonate solution were dissolved 1.46 g of (3-cyano-4-isobutoxyphenyl)boronic acid and 1.86 g of methyl 2-chloroisonicotinate, and the resulting solution was heated at 100° C. for 1 hour in the presence of 0.49 g of tetrakis(triphenylphosphine)palladium. The reaction solution was extracted with ethyl acetate and the organic layer was washed with brine and then dried and concentrated under reduced pressure. The residue was purified by silica gel column chromatography (hexane:ethyl acetate:chloroform=70:15:15) to obtain 1.98 g of methyl 2-(3-cyano-4-isobutoxyphenyl)isonicotinate.

(2) Then, 1.98 g of the compound was dissolved in a mixed solution of 30 ml of methanol and 70 ml of THF, and 9 ml of a 1M aqueous sodium hydroxide solution was added thereto, followed by heating at 50° C. for 1 hour.

After cooling, the resulting solution was neutralized with 1M hydrochloric acid and then extracted with chloroform, followed by washing with brine. After the solution was dried, concentration was performed under reduced pressure and the resulting residue was recrystallized from a mixed solvent of ethanol and water to obtain 1.66 g of 2-(3-cyano-4-isobutoxyphenyl)isonicotinic acid.

Example 2

(1) In 5 ml of DMF were dissolved 82 mg of methyl 2-(3-cyano-4-hydroxyphenyl)isonicotinate and 66 mg of isopropyl iodide, and the resulting solution was heated at 80° C. for 3 hours in the presence of 72 mg of potassium carbonate and 10 mg of tetra-n-butylammonium bromide. The reaction solution was cooled and then diluted with water, followed by extraction with ethyl acetate. The organic layer was washed with brine and then dried and concentrated under reduced pressure. The resulting residue was washed with a mixed solvent (hexane:ethyl acetate=10:1) to obtain 91 mg of methyl 2-(3-cyano-4-isopropoxyphenyl)isonicotinate.

(2) Then, 86 mg of the compound was dissolved in a mixed solution of 3 ml of methanol and 3 ml of THF, and 0.35 ml of a 1M aqueous sodium hydroxide solution was added thereto, followed by heating at 60° C. for 1 hour. After being cooled to room temperature, the resulting solution was diluted with diisopropyl ether and water and an aqueous layer was separated. The aqueous layer was neutralized with 1M hydrochloric acid and then extracted with ethyl acetate. After being washed with water, the organic layer was dried and concentrated under reduced pressure to obtain 55 mg of 2-(3-cyano-4-isopropoxyphenyl)isonicotinic acid.

Example 3

(1) In 5 ml of THF were dissolved 63 mg of 3-(methylthio)-1-propanol and 100 mg of methyl 2-(3-cyano-4-hydroxyphenyl)isonicotinate, and the resulting solution was heated at 0° C. for 10 minutes in the presence of 0.15 ml of tributylphosphine and 149 mg of 1,1'-(azodicarbonyl)dipiperidine. Then, the reaction solution was warmed to room temperature and stirred all day and night. After removal of the solvent, water was added and extraction with ethyl acetate was performed. The resulting organic layer is washed with brine and then dried and concentrated under reduced pressure. The resulting residue was purified by silica gel column chromatography (chloroform:methanol=95:5) to obtain 92 mg of methyl 2-{3-cyano-4-[3-(methylthio)propoxy]phenyl}isonicotinate.

(2) Then, 92 mg of the compound was dissolved in a mixed solution of 3 ml of methanol and 3 ml of THF, and 0.32 ml of a 1M aqueous sodium hydroxide solution was added thereto, followed by heating at 60° C. for 1 hour. After being cooled, the reaction solution was diluted with diisopropyl ether and an aqueous layer was separated. The aqueous layer was neutralized with 1M hydrochloric acid and then extracted with ethyl acetate. After washing with brine, the organic layer was dried and concentrated under reduced pressure to obtain 81 mg of 2-{3-cyano-4-[3-(methylthio)propoxy]phenyl}isonicotinic acid.

Example 4

(1) In 7 ml of DMSO was dissolved 2.22 g of methyl 2-(3-cyano-4-fluorophenyl)isonicotinate, and 2.44 ml of hexamethyleneimine was added thereto, followed by heating at 50° C. for 5 hours. After cooling, the reaction solution was diluted with ethyl acetate and was washed with 1M hydrochloric acid, a saturated aqueous sodium hydrogen carbonate solution, and brine, successively. The organic layer was dried and then concentrated under reduced pressure and the resulting residue was dissolved in a mixed solvent of ethyl acetate and diisopropyl ether. Activated carbon was added thereto, followed by stirring for 1 hour. Then, the activated carbon was removed by filtration and washed with ethyl acetate. The resulting filtrate and washing liquid were combined and concentrated to obtain 2.58 g of methyl 2-(4-azepan-1-yl-3-cyanophenyl)isonicotinate.

(2) Then, 2.49 g of the compound was dissolved in a mixed solvent of 15 ml of methanol and 30 ml of THF, and 11 ml of a 1M aqueous sodium hydroxide solution was added thereto, followed by heating at 80° C. for 1 hour.

After cooling, the reaction solution was concentrated under reduced pressure. Then, water was added, followed by washing with diisopropyl ether. The resulting aqueous layer was filtered and then neutralized with 1M hydrochloric acid. The precipitated crystals were collected by filtration and washed with water and ethanol, successively. The crude crystals were recrystallized from a mixed solvent of DMSO and water to obtain 2.07 g of a free compound of 2-(4-azepan-1-yl-3-cyanophenyl)isonicotinate. 295 mg of the free compound obtained in a similar manner was suspended in a mixed solvent of 4 ml of ethanol and 2 ml of THF, and 0.46 ml of a 4M hydrogen chloride-ethyl acetate solution was added thereto. After stirring at room temperature for 30 minutes, the precipitated crystals were collected by filtration to obtain 279 mg of 2-(4-azepan-1-yl-3-cyanophenyl)isonicotinic acid monohydrochloride.

Example 5

(1) In 0.4 ml of 1,4-dioxane were dissolved 237 mg of methyl 2-(3-cyano-4-{[(trifluoromethyl)sulfonyl]oxy}phenyl)-isonicotinate and 0.4 ml of heptamethyleneimine, followed by heating at 90° C. for 1 hour. After the reaction solution was cooled, purification by silica gel column chromatography (hexane:ethyl acetate:chloroform=80:10:10) was performed to obtain 23 mg of 2-(4-azocan-1-yl-3-cyanophenyl)isonicotinate.

(2) Then, 22 mg of the compound was dissolved in a mixed solution of 2 ml of methanol and 2 ml of THF, and 0.15 ml of a 1M aqueous sodium hydroxide solution was added thereto, followed by reaction at room temperature for 20 hours. To the reaction solution were added 0.15 ml of 1M hydrochloric acid and 20 ml of water, and the resulting precipitate was collected by filtration. The precipitate was washed with water and then dried to obtain 16 mg of 2-(4-azocan-1-yl-3-cyanophenyl) isonicotinic acid.

Example 6

(1) In 3 ml of DMSO was dissolved 247 mg of methyl 2-(3-cyano-4-fluorophenyl)isonicotinate, and 0.31 ml of aminomethylcyclohexane was added thereto. After being stirred at 40° C. for 17 hours, the reaction solution was diluted with ethyl acetate and washed with water and brine, successively. The organic layer was dried and concentrated under reduced pressure and then recrystallization was performed from a mixed solvent of diisopropyl ether and hexane to obtain 266 mg of methyl 2-{3-cyano-4-[(cyclohexylmethyl)amino] phenyl}isonicotinate.

(2) Then, 266 mg of the compound was dissolved in a mixed solvent of 5 ml of methanol and 10 ml of THF, and 1.14 ml of a 1M aqueous sodium hydroxide solution was added thereto, followed by heating at 80° C. for 1 hour. After cooling, the reaction solution was diluted with water and washed with diethyl ether. The resulting aqueous layer was neutralized with 1M hydrochloric acid and extracted with ethyl acetate and the organic layer was dried and concentrated under reduced pressure. The resulting residue was recrystallized from a mixed solvent of ethanol and water to obtain 199 mg of 2-{3-cyano-4-[(cyclohexylmethyl)amino]phenyl}isonicotinic acid. Then, 199 mg of the compound was dissolved in 10 ml of ethanol and 0.59 ml of a 1M aqueous sodium hydroxide solution was added thereto. After stirring at room temperature for 15 minutes, the reaction solution was concentrated. The resulting residue was washed with 2-propanol to obtain 181 mg of sodium 2-{3-cyano-4-[(cyclohexylmethyl)amino]phenyl}isonicotinate.

Example 7

Using [3-cyano-4-(isobutylthio)phenyl]boronic acid and methyl 2-chloroisonicotinate, 2-[3-cyano-4-(isobutylthio)phenyl]isonicotinic acid was obtained according to the method of Example 1. Then, 346 mg of the resulting 2-[3-cyano-4-(isobutylthio)phenyl]isonicotinic acid was suspended in 30 ml of ethanol, and 1.11 ml of a 1M aqueous sodium hydroxide solution was added to the suspension, followed by stirring at room temperature for 15 minutes. The reaction solution was concentrated under reduced pressure and the residue was washed with 2-propanol and subsequently with diethyl ether to obtain 208 mg of sodium 5-[3-cyano-4-(isobutylthio)phenyl]isonicotinate.

Example 8

Using methyl 2-(3-cyano-4-hydroxyphenyl)isonicotinate and cyclobutylmethyl bromide, 2-[3-cyano-4-(cyclobutylmethoxy)phenyl]isonicotinic acid was obtained according to the method of Example 2. Then, 150 mg of the compound was suspended in 5 ml of methanol, and 32 mg of sodium methoxide was added to the suspension at 0° C., followed by stirring for 3 hours with gradual elevation of the temperature to room temperature. The reaction solution was concentrated under reduced pressure to obtain 115 mg of sodium 2-[3-cyano-4-(cyclobutylmethoxy)phenyl]isonicotinate.

Examples 9 to 84

The compounds of Examples 9 to 84 shown in the following Tables 4 to 8 were produced in a similar manner to the methods of Examples 1, 2, 4, 5, 6, 7, and 8, using corresponding starting materials, respectively.

The structures and physicochemical data of the compounds of Examples 9 to 84 are shown in Tables 3 to 8. In this connection, the numerals in parenthesis attached to Example No. (Ex) in the tables represent step numbers at which the compounds were produced. For example, the structure and physicochemical data of the compound of Example 1(1) in Table 3 represent those of the intermediate obtained in step (1) in Example 1.

Moreover, Tables 9 and 10 show the structures of other compounds of the invention. They can be easily synthesized by the above production methods, the methods described in Examples, and methods obvious to those skilled in the art or by the use of modified methods thereof.

TABLE 2

| REx | Str | Dat |
|---|---|---|
| 13 | 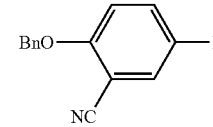 | EI: 287, 289 |
| 14 | 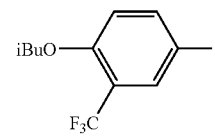 | F: 298 |
| 15 | 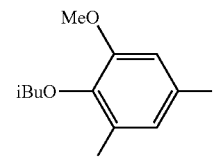 | F: 284 |
| 16 | 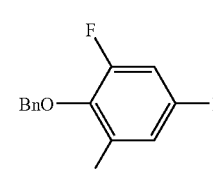 | EI: 215, 217 |
| 17 | 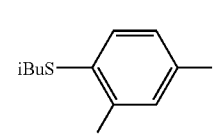 | EI: 269, 271 |
| 18 | 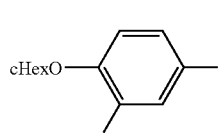 | EI: 279, 281 |
| 19 | 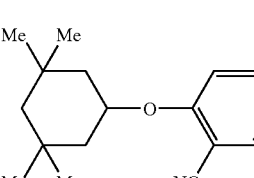 | F: 336, 338 |
| 20 | 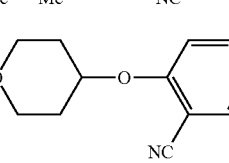 | F: 282, 284 |
| 21 | 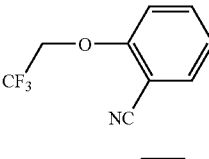 | EI: 279, 281 |
| 22 | 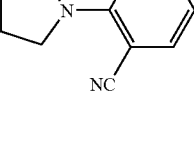 | F: 251 |

TABLE 2-continued

| REx | Str | Dat |
|---|---|---|
| 23 | BnO-C6H3(CN)-B(OH)2 | ES: 254 |
| 24 | tBuCH2O-C6H3(CN)-B(OH)2 | FN: 232 |
| 25 | iBuO-C6H3(CF3)-B(OH)2 | FN: 261 |
| 26 | MeO, iBuO-C6H2(CN)-B(OH)2 | F: 306(G-2W) |
| 27 | PhO-C6H3(CN)-B(OH)2 | F: 296(G-2W) |
| 28 | iBuS-C6H3(CN)-B(OH)2 | F: 235 |
| 29 | cHexO-C6H3(CN)-B(OH)2 | FN: 244 |
| 30 | 3,3,5,5-tetramethylcyclohexyl-O-C6H3(CN)-B(OH)2 | F: 358(G-2W) |
| 31 | CF3CH2O-C6H3(CN)-B(OH)2 | F: 302(G-2W) |
| 32 | tetrahydropyran-4-yl-O-C6H3(CN)-B(OH)2 | F: 304(G-2W) |
| 33 | piperidin-1-yl-C6H3(CN)-B(OH)2 | ES: 231 |
| 34 | pyrrolidin-1-yl-C6H3(CN)-B(OH)2 | ES: 217 |
| 35 | BnO-C6H2(F)(CN)-B(OH)2 | F: 328(G-2W) |

TABLE 3

| Ex | Str | Dat |
|---|---|---|
| 1(1) | iBuO-C6H3(CN)-pyridine-CO2Me | F: 311; NMRC: 3.91(2H, d), 4.04(3H, s) 7.06(1H, d) |
| 2(1) | iPrO-C6H3(CN)-pyridine-CO2Me | F: 297; NMRC: 1.45(6H, d), 4.00(3H, s), 7.08(1H, d) |

TABLE 3-continued

| Ex | Str | Dat |
|---|---|---|
| 3(1) | MeS-CH₂CH₂-O-C₆H₃(CN)-pyridine-CO₂Me | F: 343; NMRC: 2.77(2H, t), 4.00(3H, s), 7.09(1H, d) |
| 4(1) | azepane-N-C₆H₃(CN)-pyridine-CO₂Me | F: 336; NMRC: 3.72(4H, dd), 3.99(3H, s), 6.92(1H, d) |
| 5(1) | azocane-N-C₆H₃(CN)-pyridine-CO₂Me | F: 350; NMRC: 3.81(4H, dd), 4.00(3H, s), 6.90(1H, d) |
| 6(1) | cyclohexyl-CH₂-NH-C₆H₃(CN)-pyridine-CO₂Me | F: 350; NMR: 3.11(2H, dd), 3.93(3H, s), 6.90(1H, d) |

TABLE 4

$R^7-X-C_6H_3(R^5)$-pyridine-COOH

| Ex | Syn | R⁷—X | R⁵ | Dat |
|---|---|---|---|---|
| 1 | 1 | iBuO— | CN | F: 297; NMR: 4.00(2H, d), 7.38(1H, d), 7.77(1H, dd) |
| 2 | 2 | iPrO— | CN | F: 283; NMR: 1.36(6H, d), 7.41(1H, d), 8.83(1H, d) |
| 3 | 3 | MeS—(CH₂)₃—O— | CN | F: 329; NMR: 4.31(2H, t), 7.40(1H, d), 8.83(1H, d) |
| 9 | 1 | BnO— | CN | F: 331; NMR: 5.34(2H, s), 7.71(1H, d), 8.39(1H, d) |
| 10 | 1 | piperidin-1-yl | CN | F: 308; NMR: 3.20-3.28(4H, m), 7.24(1H, d), 7.75(1H, dd) |
| 11 | 1 | pyrrolidin-1-yl | CN | F: 294; NMR: 3.53-3.69(4H, m), 6.88(1H, d), 7.67(1H, dd) |
| 12 | 1 | tBu—CH₂—O— | CN | F: 311; NMR: 3.89(2H, s), 7.37(1H, d), 8.83(1H, d) |
| 13 | 1 | CF₃—CH₂—O— | CN | F: 323; NMR: 5.09(2H, q), 7.53(1H, d), 7.80(1H, dd) |
| 14 | 1 | tetrahydropyran-4-yl-O— | CN | F: 325; NMR: 3.82-3.94(2H, m), 7.49(1H, d), 7.77(1H, dd) |
| 15 | 2 | cPenO— | CN | F: 309; NMR: 5.10(1H, m), 7.38(1H, d), 8.83(1H, d) |

TABLE 4-continued

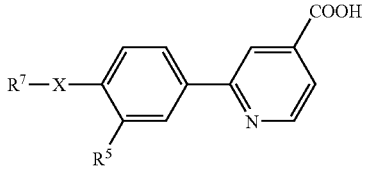

| Ex | Syn | R⁷—X | R⁵ | Dat |
|---|---|---|---|---|
| 16 | 2 | iPenO— | CN | ES: 311; NMR: 4.25(2H, t), 7.41(1H, d), 8.83(1H, d) |
| 17 | 2 | EtO— | CN | F: 269 ; NMR: 1.41(3H, t), 7.37(1H, d), 8.83(1H, d) |
| 18 | 2 | nBuO— | CN | F: 297; NMR: 4.23(2H, t), 7.39(1H, d), 8.83(1H, d) |
| 19 | 2 | 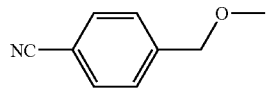 | CN | F: 334, NMR 6 01(2H, t), 7.33(1H, d), 8.83(1H, d) |
| 20 | 2 | nPrO— | CN | F: 283; NMR: 4.19(2H, t), 7.38(1H, d), 7.77(1H, dd) |
| 21 | 2 | 2Py-CH₂—O— | CN | F: 332; NMR: 5.45(2H, s), 8.35(1H, s), 8.82(1H, d) |
| 22 | 2 | 3Py-CH₂—O— | CN | F: 332; NMR: 5.43(2H, s), 8.36(1H, s), 8.83(1H, s) |
| 23 | 2 | iBuO— | CF₃ | F: 340; NMR: 3.98(2H, d), 7.37(1H, d), 7.76(1H, dd) |
| 24 | 2 | MeO— | CN | F: 255; NMR: 4.00(3H, s), 7.39(1H, d), 7.77(1H, dd) |
| 25 | 2 | nPenO— | CN | F: 311; NMR: 4.22(2H, t), 7.38(1H, d), 7.77(1H, dd) |
| 26 | 2 | nHexO— | CN | F: 325; NMR: 4.21(2H, t), 7.37(1H, d), 7.77(1H, dd) |
| 27 | 2 | (Et)₂CHCH₂O— | CN | F: 325; NMR: 4.13(2H, d), 7.41(1H, d), 7.77(1H, dd) |
| 28 | 2 | MeO(CH₂)₃O— | CN | F: 313; NMR: 3.53(2H, t), 7.39(1H, d), 7.77(1H, dd) |
| 29 | 2 | (Et)₂CHO— | CN | F: 311; NMR: 0.95(6H, t), 7.41(1H, d), 7.77(1H, dd) |
| 30 | 2 | PhOCH₂CH₂O— | CN | F: 361; NMR: 4.34-4.43(2H, m), 7.31(2H, t), 7.78(1H, dd) |

TABLE 5

| 31 | 2 | MeOCH₂CH₂O— | CN | F: 299; NMR: 3.36(3H, s), 7.41(1H, d), 7.77(1H, dd) |
|---|---|---|---|---|
| 32 | 2 | 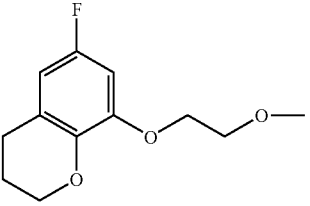 | CN | F: 356; NMR: 7.46(1H, d), 7.78(1H, dd), 7.94(2H, d) |
| 33 | 2 | 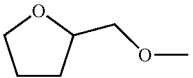 | CN | F: 435; NMR: 6.52(1H, dd), 7.48(1H, d), 7.78(1H, dd) |
| 34 | 2 | NC—(CH₂)₃—O— | CN | F: 308; NMR: 2.70(2H, t), 7.42(1H, d), 7.78(IH, dd) |
| 35 | 2 | cHex-CH₂—O— | CN | F: 337; NMR: 4.03(2H, d), 7.37(1H, d), 7.77(1H, dd) |
| 36 | 2 | HO₂C—CH₂—O— | CN | F: 299; NMR: 4.99(2H, s), 7.29(1H, d), 7.77(1H, dd) |
| 37 | 2 | H₂N(OC)CH₂O— | CN | F: 298; NMR: 4.77(2H, s), 7.21(1H, d), 7.77(1H, d) |
| 38 | 2 | BnO—(CH₂)₃—O— | CN | F: 389; NMR: 4.51(2H, s), 7.39(1H, d), 7.77(1H, dd) |
| 39 | 2 | 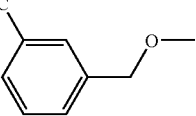 | CN | F: 325; NMR: 3.71(1H, q), 7.40(1H, d), 7.77(1H, dd) |
| 40 | 2 | cHexO— | CN | F: 323; NMR: 4.65-4.74(1H, m), 7.43(1H, d), 7.75(1H, dd) |
| 41 | 2 | (Me)₂N(CO)CH₂O— | CN | F: 326; NMR: 2.86(3H, s), 7.24(1H, d), 7.77(1H, d) |
| 42 | 2 | PhO— | CN | F: 317; NMR: 7.25(2H, d), 7.52(2H, t), 7.80(1H, dd) |
| 43 | 2 |  | CN | F: 356; NMR: 5.43(2H, s), 7.46(1H, d), 8.58(1H, d) |

TABLE 5-continued

| 44 | 2 | 3,3,5,5-tetramethylcyclohexyl methyl ether | CN | FN: 377; NMR: 4.86-4.96(1H, m), 7.42(1H, d), 8.83(1H, d) |

TABLE 6

Structure: R⁷—X—(phenyl with CN)—(pyridine with COOH)

| Ex | Syn | R⁷—X | Sal | Dat |
|---|---|---|---|---|
| 4 | 4 | N-methylazepane | HCl | F: 322; NMR: 3.71(4H, dd), 7.09(1H, d), 8.20(1H, dd) |
| 5 | 5 | N-methylazocane | | F: 336; NMR: 3.78(4H, dd), 7.07(1H, d), 7.68(1H, dd) |
| 6 | 6 | cHex-CH$_2$—NH— | Na | F: 358(Na); NMR: 3.09(2H, dd), 6.87(1H, d), 7.58(1H, dd) |
| 7 | 7 | iBuS— | Na | F: 335(Na); NMR: 3.07(2H, d), 7.65-7.70(2H, m), 8.24(1H, s) |
| 8 | 8 | cBu-CH$_2$—O— | Na | F: 309; NMR: 4.19(2H, d), 7.36(1H, d), 7.66(1H, dd) |
| 45 | 4 | 4-methyl-1-methylpiperidine | HCl | F: 322; NMR: 0.98(3H, d), 7.78(1H, dd), 8.43(1H, d) |
| 46 | 5 | morpholine | | FN: 308; NMR: 3.79(4H, dd), 7.28(1H, d), 7.76(1H, dd) |
| 47 | 5 | 1-methyl-3-(N,N-diethylcarbamoyl)piperidine | | F: 407; NMR: 1.01(3H, t), 7.27(1H, d), 7.75(1H, dd) |
| 48 | 5 | (2R,6S)-2,6-dimethyl-4-methylmorpholine | | F: 338; NMR: 1.16(6H, d), 7.26(1H, d), 7.76(1H, dd) |
| 49 | 5 | 1-methyl-1,2,3,6-tetrahydropyridine | | F: 306; NMR: 5.79-5.96(2H, m), 7.24(1H, d), 7.74(1H, dd) |
| 50 | 5 | 1-(ethoxycarbonyl)-4-methylpiperazine | | F: 381; NMR: 1.22(3H, t), 7.28(1H, d), 8.83(1H, d) |

TABLE 6-continued

Structure: R⁷—X—[benzene with CN]—[pyridine]—COOH

| Ex | Syn | R⁷—X | Sal | Dat |
|---|---|---|---|---|
| 51 | 6 | 4-fluoro-1-methylpiperidinyl | Na | F: 326; NMR: 3.19-3.28(2H, m), 7.28(1H, d), 7.65(1H, dd) |
| 52 | 6 | nPr—NH— | Na | F: 304(Na); NMR: 3.20(2H, dt), 6.37,(1H, t), 6.88(1H, d) |
| 53 | 6 | Ph-CH₂CH₂-N(Me)— | Na | F: 380 NMR: 3.68(2H, dd), 7.13(1H, d), 7.60(1H, d) |

TABLE 7

Structure: R⁷—X—[benzene with CN]—[pyridine]—COOH

| Ex | Syn | R⁷—X | Sal | Dat |
|---|---|---|---|---|
| 54 | 6 | iBu—NH— | Na | F: 318(Na); NMR: 3.07(2H, dd), 6.39(1H, t), 6.88(1H, d) |
| 55 | 6 | cPen-NH— | Na | F: 330(Na); NMR: 3.87-3.99(1H, m), 5.96(1H, d), 6.92(1H,d) |
| 56 | 6 | nBu—NH— | Na | F: 318(Na); NMR: 3.23(2H, dt), 6.87(1H, d), 7.58(1H, d) |
| 57 | 6 | nBu—N(Me)— | Na | F: 332(Na); NMR: 3.45(2H, dd), 7.11(1H, d), 7.60(1H, d) |
| 58 | 6 | Et₂CH-CH₂-NH(Me) | Na | F: 346(Na); NMR: 3.14(2H, dd), 6.87(1H, d), 7.58(1H, d) |
| 59 | 6 | 3-methyl-1-methylpiperidinyl | Na | F: 322; NMR: 2.81(1H, dt), 7.22(1H, d), 7.64(1H, dd) |
| 60 | 6 | nHex-N(Me)— | Na | F: 338; NMR: 3.44(2H, dd), 7.09(1H, d), 7.62(1H, dd) |
| 61 | 6 | cOct-NH— | Na | F: 350; NMR: 3.65-3.76(1H, m), 6.86(1H, d), 7.56(1H, dd) |
| 62 | 6 | cHex-NH— | Na | F: 322; NMR: 3.40-3.53(1H, m), 6.93(1H, d), 7.59(1H, dd) |
| 63 | 6 | cHep-NH— | Na | F: 336; NMR: 3.61-3.72(1H, m), 6.85(1H, d), 7.58(1H, d) |
| 64 | 6 | nPen-CH(Me)—NH— | Na | F: 338; NMR: 3.61-3.72(1H, m), 6.89(1H, d), 7.59(1H, d) |
| 65 | 6 | nBu-N(Et)— | Na | F: 346(Na); NMR: 3.47(2H, q), 7.13(1H, d), 7.61(1H, dd) |
| 66 | 6(1) 5(2) | 4-methylcyclohexyl-(4-methylpiperazin-1-yl) | | APN: 403; NMR: 0.94(3H, d), 7.31(1H, d), 8.83(1H, d) |
| 67 | 6(1) 5(2) | 4-methoxy-4-cyclohexyl-1-methylpiperidinyl | | APN: 418; NMR: 3.09(3H, s), 7.74(1H, dd), 8.43(1H, d) |
| 68 | 6(1) 5(2) | 4-(cyclohexylmethoxy)-1-methylpiperidinyl | | APN: 418; NMR: 3.26(2H, d), 7.26(1H, d), 8.44(1H, d) |

TABLE 7-continued
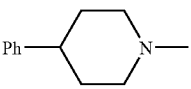
| Ex | Syn | R⁷—X | Sal | Dat |
|---|---|---|---|---|
| 69 | 6(1) 5(2) | Ph-piperidine-N-Me | | APN: 382; NMR: 3.79(2H, d), 7.27(1H, d), 8.83(1H, dd) |
| 70 | 6(1) 5(2) | isoindoline-N- | | APN: 340; NMR: 5.08(4H, s), 7.03(1H, d), 7.69(1H, dd) |
| 71 | 8 | 2-CN-benzyl-OCH₂- | Na | F: 356; NMR: 5.51(2H, s), 7.97(1H, d), 8.57(1H, d) |
| 72 | 8 | (Me)₂C=CCHCH₂—O— | Na | F: 309; NMR: 5.49(1H, t), 7.37(1H, d), 7.66(1H, d) |
TABLE 8
| Ex | Syn | Str | Dat |
|---|---|---|---|
| 73 | 1 | 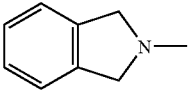 | F: 311; NMR: 2.62(3H, s), 3.99(1H, d), 7.35(1H, d) |
| 74 | 1 | 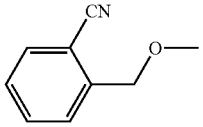 | F: 331; NMR: 4.01(2H, d), 7.38(1H, d), 7.77(1H, s) |
| 75 | 1 | 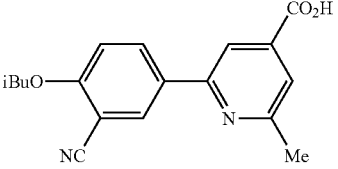 | F: 315; NMR: 4.02(2H, d), 7.42(1H, d), 8.63(1H, d) |
| 76 | 1 | 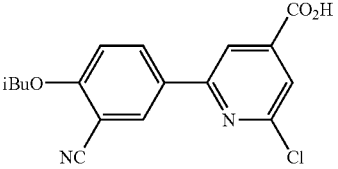 | F: 315; NMR: 4.00(2H, d), 7.37(1H, d), 8.31(1H, d) |

TABLE 8-continued

| Ex | Syn | Str | Dat |
|----|-----|-----|-----|
| 77 | 1 | iBuO, NC substituents on phenyl; pyridine with CO2H and Cl | F: 331; NMR: 4.00(2H, d), 7.37(1H, d), 8.80(1H, s) |
| 78 | 2 | MeO, iBuO, NC substituents on phenyl; pyridine with CO2H | F: 327; NMR: 3.32(3H, s), 7.81(1H, dd), 8.42(1H, s) |
| 79 | 2 | Br, iBuO, NC substituents on phenyl; pyridine with CO2H | FN: 375; NMR: 4.04(2H, d), 7.83(1H, dd), 8.46(1H, s) |
| 80 | 2 | Cl, iBuO, NC substituents on phenyl; pyridine with CO2H | FN: 329; NMR: 4.05(2H, d), 7.84(1H, dd), 8.47(1H, s) |
| 81 | 2 | Br, nPrO, NC substituents on phenyl; pyridine with CO2H | F: 361; NMR: 4.20(2H, t), 7.84(1H, dd), 8.61(1H, dd) |
| 82 | 7 | iBuO, NC substituents on phenyl; pyridine with Cl and CO2Na | F: 331; NMR: 3.99(2H, d), 7.13(1H, d), 7.34(1H, d) |
| 83 | 8 | Br, (Et)2CHCH2O, NC substituents on phenyl; pyridine with CO2Na | F: 405; NMR: 4.12(2H, d), 7.73(1H, d), 8.45(1H, d) |
| 84 | 8 | F, iBuO, NC substituents on phenyl; pyridine with CO2Na | FN: 313; NMR: 4.13(2H, d), 7.69(1H, dd), 8.60(1H, dd) |

TABLE 9
| No | Str |
|---|---|
| 1 | 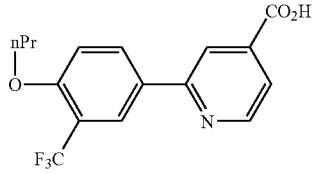 |
| 2 | 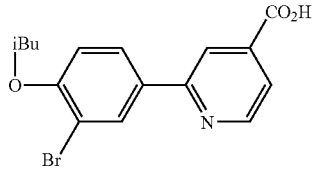 |
| 3 | 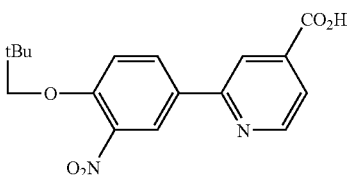 |
| 4 | 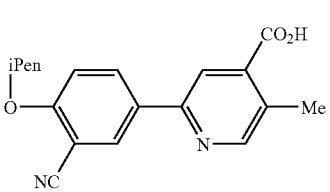 |
| 5 | 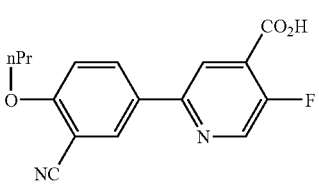 |
| 6 | 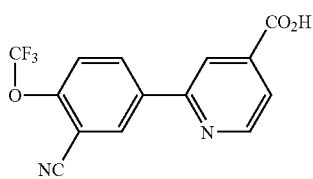 |
| 7 | 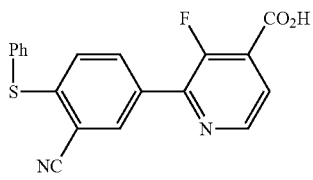 |
| 8 | 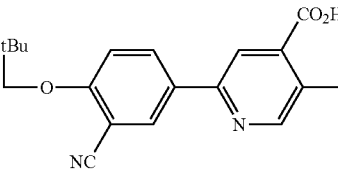 |
TABLE 9-continued
| No | Str |
|---|---|
| 9 | 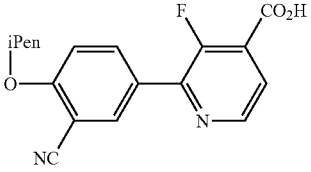 |
| 10 | 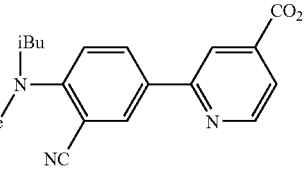 |
| 11 | 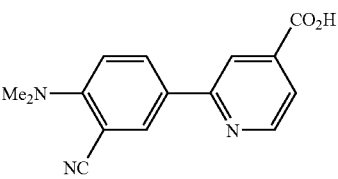 |
| 12 | 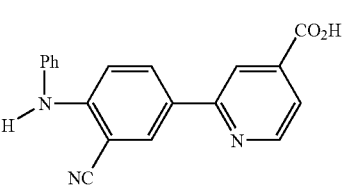 |
| 13 | 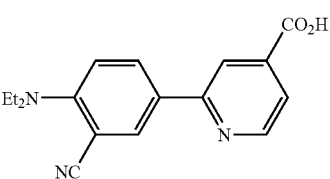 |
| 14 | 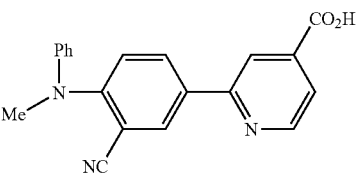 |
| 15 | 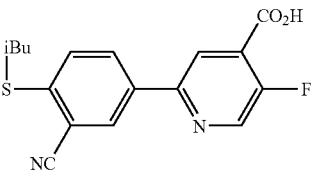 |
| 16 | 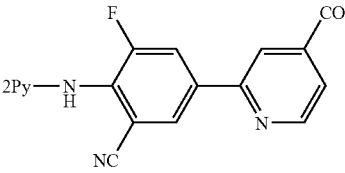 |

TABLE 9-continued
| No | Str |
|----|-----|
| 17 | 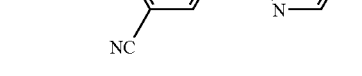 |
| 18 | 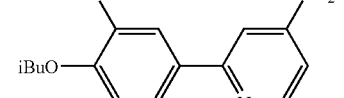 |
| 19 |  |
| 20 | 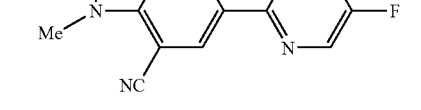 |
| 21 | 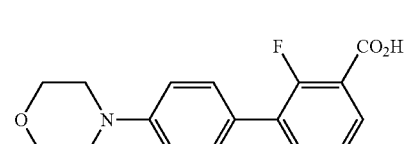 |
| 22 | 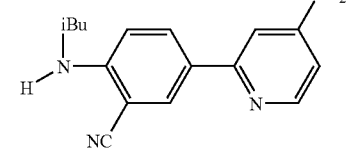 |
| 23 | 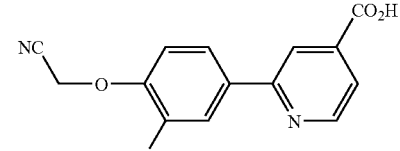 |
| 24 | 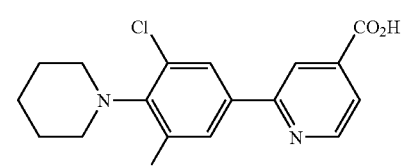 |
TABLE 9-continued
| No | Str |
|----|-----|
| 25 | 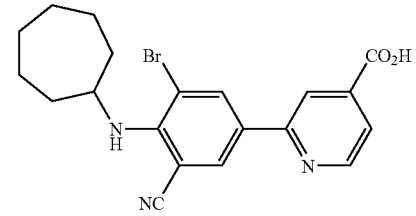 |
| 26 | 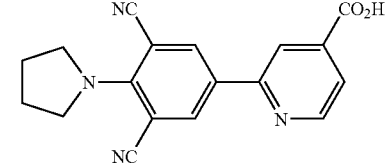 |
| 27 | 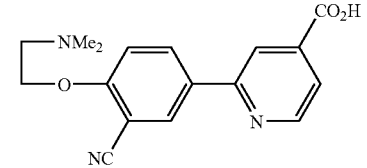 |
TABLE 10
| No | Str |
|----|-----|
| 31 | 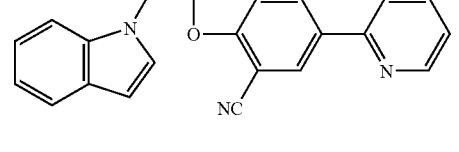 |
| 32 | 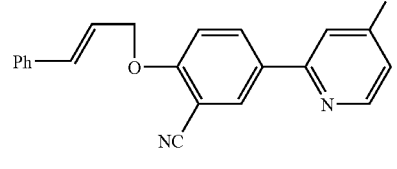 |
| 33 | 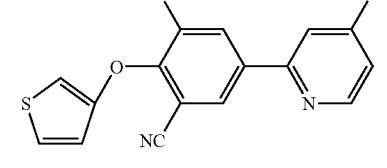 |
| 34 | 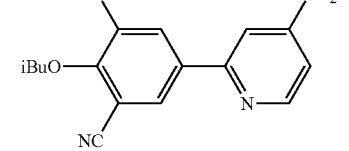 |

TABLE 10-continued
| No | Str |
|----|-----|
| 35 |  |
| 36 | 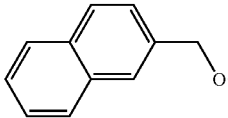 |
| 37 | |
| 38 | |
| 39 | |
| 40 | |
| 41 | |
| 42 | |
| 43 |  |
| 44 | |
| 45 | 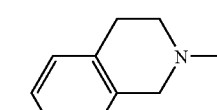 |
| 46 | |
| 47 | |
| 48 | 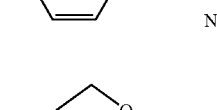 |
| 49 | 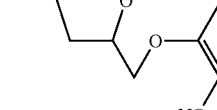 |
| 50 | |
INDUSTRIAL APPLICABILITY
Since the compound of the present invention has a strong xanthine oxidase-inhibitory action, the compound is useful as a therapeutic or preventive drug for hyperuricemia, gout, uric acid urolithiasis, renal dysfunction accompanied by hyperuricemia, inflammatory bowel diseases (ulcerative colitis, Crohn's disease), diabetic kidney diseases, diabetic retinopathy, organ damage at organ transplantation or ischemic reperfusion, tumor lysis syndrome, heart failure, and cerebrovascular disorder, particularly hyperuricemia, gout, inflammatory bowel diseases, diabetic kidney diseases, and diabetic retinopathy.

The invention claimed is:

1. A compound represented by the formula ($I^4$) or a salt thereof:

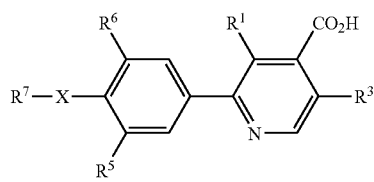

wherein the symbols have the following meanings:
$R^1$: H or halogen,
$R^3$: H or lower alkyl,
$R^5$: —CN,
$R^6$: H or halogen,
X: —O—, —N($R^8$)—, or —S—,
$R^8$: H or lower alkyl
$R^7$: linear or branched alkyl having 1 to 8 carbon atoms, linear or branched alkenyl having 3 to 8 carbon atoms,
—Y-(cycloalkyl which may contain an oxygen atom),
—Y-phenyl, or —Y-monocyclic heteroaryl,
where the linear or branched alkyl having 1 to 8 carbon atoms and linear or branched alkenyl having 3 to 8 carbon atoms may be substituted with one to three groups selected from the group consisting of —CN, —O-lower alkyl, —S-lower alkyl, and halogen, which may be the same or different from each other; the cycloalkyl which may contain an oxygen atom, phenyl, and monocyclic heteroaryl may be substituted with one to four groups selected from the group consisting of —CN, halogen, and lower alkyl, which may be the same or different from each other, Y: bond, lower alkylene, lower alkenylene, or -(lower alkylene)-O—,
where, when X is a group represented by —N($R^8$)—, $R^8$ and $R^7$ are combined together with the adjacent nitrogen atom to form a nitrogen-containing saturated heterocycle and the nitrogen-containing saturated heterocycle may be substituted with one or two groups selected from the group consisting of lower alkyl, —O-lower alkyl, —CON(lower alkyl)$_2$, —CO$_2$-lower alkyl, halogen, phenyl, (cycloalkyl which may be substituted with lower alkyl), and —O-lower alkylene-cycloalkyl, which may be the same or different from each other.

2. The compound according to claim 1 or a salt thereof, wherein X is —O—.

3. The compound according to claim 1 or a salt thereof, wherein X is —N($R^8$)—.

4. The compound according to claim 2 or a salt thereof, wherein $R^7$ is a linear or branched alkyl group having 2 to 6 carbon atoms.

5. The compound according to claim 3 or a salt thereof, wherein $R^8$ and $R^7$ are combined together with the adjacent nitrogen atom to form a nitrogen-containing saturated heterocycle which may be substituted with lower alkyl.

6. The compound according to claim 1 selected from the group consisting of 2-(3-cyano-4-isobutoxyphenyl)isonicotinic acid, 2-(3-cyano-4-piperidin-1-ylphenyl)isonicotinic acid, 2-{3-cyano-4-[(3,3,5,5-tetramethylcyclohexyl)oxy]phenyl} isonicotinic acid, 2-(4-azepan-1-yl-3-cyanophenyl)isonicotinic acid, 2-[3-cyano-4-(isobutylthio)phenyl]isonicotinic acid, 2-[3-cyano-4-(4-methylpiperidin-1-yl)phenyl]isonicotinic acid, 2-[3-cyano-4-(4-fluoropiperidin-1-yl)phenyl]isonicotinic acid, [hexyl(methyl)amino]phenyl} isonicotinic acid, 2-[3-cyano-4-(cyclohexylamino)phenyl]isonicotinic acid, 2-[3-cyano-4-(cycloheptylamino)phenyl]isonicotinic acid, and 2-(3-cyano-5-fluoro-4-isobutoxyphenyl)isonicotinic acid, or a pharmaceutically acceptable salt thereof.

7. A pharmaceutical composition comprising the compound according to claim 1 or a pharmaceutically acceptable salt thereof and a pharmaceutically acceptable carrier.

8. The pharmaceutical composition according to claim 7, wherein the composition has activity for inhibiting xanthine oxidase.

* * * * *

UNITED STATES PATENT AND TRADEMARK OFFICE
CERTIFICATE OF CORRECTION

PATENT NO. : 7,820,700 B2
APPLICATION NO. : 11/661284
DATED : October 26, 2010
INVENTOR(S) : Junji Miyata et al.

It is certified that error appears in the above-identified patent and that said Letters Patent is hereby corrected as shown below:

Column 48, lines 24-37 currently reads:

6. The compound according to claim 1 selected from the group consisting of 2-(3-cyano-4-isobutoxyphenyl)isonicotinic acid, 2-(3-cyano-4-piperidin-1-ylphenyl)isonicotinic acid, 2-{3-cyano-4-[(3,3,5,5-tetramethylcyclohexyl)oxy]phenyl}isonicotinic acid, 2-(4-azepan-1-yl-3-cyanophenyl)isonicotinic acid, 2-[3-cyano-4-(isobutylthio)phenyl]isonicotinic acid, 2-[3-cyano-4-(4-methylpiperidin-1-yl)phenyl]isonicotinic acid, 2-[3-cyano-4-(4-fluoropiperidin-1-yl)phenyl]isonicotinic acid, hexyl(methyl)amino]phenyl}isonicotinic acid, 2-[3-cyano-4-(cyclohexylamino)phenyl]isonicotinic acid, 2-[3-cyano-4-(cycloheptylamino)phenyl]isonicotinic acid, and 2-(3-cyano-5-fluoro-4-isobutoxyphenyl)isonicotinic acid, or a pharmaceutically acceptable salt thereof.

and should read:

6. The compound according to claim 1 selected from the group consisting of 2-(3-cyano-4-isobutoxyphenyl)isonicotinic acid, 2-(3-cyano-4-pipcridin-l-ylphenyl)isonicotinic acid, 2-{3-cyano-4-[(3,3,5,5-tetramethylcyclohexyl)oxy]phenyl}isonicotinic acid, 2-(4-azepan-1-yl-3-cyanophenyl)isonicotinic acid, 2-[3-cyano-4-(isobutylthio)phenyl]isonicotinic acid, 2-[3-cyano-4-(4-methylpiperidin-1-yl)phenyl]isonicotinic acid, 2-[3-cyano-4-(4-fluoropiperidin-1-yl)phenyl]isonicotinic acid, 2-[3-cyano-4-(isobutylamino)phenyl]isonicotinic acid, 2-{3-cyano-4-[hexyl(methyl)amino]phenyl}isonicotinic acid, 2-[3-cyano-4-(cyclohexylamino)phenyl]isonicotinic acid, 2-[3-cyano-4-(cycloheptylamino)phenyl]isonicotinic acid, and 2-(3-cyano-5-fiuoro-4-isobutoxyphenyl)isonicotinic acid, or a pharmaceutically acceptable salt thereof.

Signed and Sealed this
Twenty-second Day of March, 2011

David J. Kappos
*Director of the United States Patent and Trademark Office*